(12) United States Patent
Rabito

(10) Patent No.: US 6,440,389 B1
(45) Date of Patent: Aug. 27, 2002

(54) FLUORESCENT AGENTS FOR REAL-TIME MEASUREMENT OF ORGAN FUNCTION

(75) Inventor: Carlos Rabito, Chelsea, MA (US)

(73) Assignee: The General Hospital Corporation, Boston, MA (US)

(*) Notice: Subject to any disclaimer, the term of this patent is extended or adjusted under 35 U.S.C. 154(b) by 0 days.

(21) Appl. No.: 09/631,138

(22) Filed: Aug. 2, 2000

Related U.S. Application Data

(60) Provisional application No. 60/219,362, filed on Jul. 19, 2000.

(51) Int. Cl.$^7$ .............................................. A61B 10/00
(52) U.S. Cl. ....................................................... 424/9.6
(58) Field of Search .............................. 424/9.6, 9.61, 424/9.1; 600/317

(56) References Cited

U.S. PATENT DOCUMENTS

| | | | |
|---|---|---|---|
| 4,243,880 A | 1/1981 | Ekins et al. | 250/252.1 |
| 4,374,120 A | 2/1983 | Soini et al. | 436/546 |
| 4,428,744 A | 1/1984 | Edelson | 604/6 |
| 4,808,541 A | 2/1989 | Mikola et al. | 436/501 |
| 4,882,142 A | 11/1989 | Simon et al. | 424/1.22 |
| 4,968,631 A | 11/1990 | Dakubu | 436/501 |
| 4,976,950 A | 12/1990 | Simon et al. | 424/1.1 |
| 5,021,236 A | 6/1991 | Gries et al. | 424/9 |
| 5,301,673 A | 4/1994 | Rabito et al. | 128/659 |
| 5,316,909 A | 5/1994 | Xu | 435/6 |
| 5,468,467 A | 11/1995 | Tweedle et al. | 424/9.361 |
| 5,595,725 A | 1/1997 | Gries et al. | 424/9.34 |
| 5,603,917 A | 2/1997 | Tweedle et al. | 424/9.3 |
| 5,627,036 A * | 5/1997 | Reutelingsperger | 435/7.21 |
| 5,647,363 A * | 7/1997 | Rabito et al. | 128/659 |
| 5,660,991 A | 8/1997 | Lakowitz et al. | 435/7.1 |
| 5,811,526 A | 9/1998 | Davidson | 530/391.3 |
| 5,928,625 A * | 7/1999 | Dorshow et al. | 424/9.1 |
| 5,928,627 A * | 7/1999 | Kiefer et al. | 424/9.6 |

FOREIGN PATENT DOCUMENTS

| | | |
|---|---|---|
| EP | 0 103 558 | 3/1984 |
| WO | WO 93/11802 | 6/1993 |
| WO | WO 97/40055 | 10/1997 |

OTHER PUBLICATIONS

Aime, et al., "MRI Contrast Agents: Macrocylic Lanthanide (III) Complexes with Improved Relaxation Efficiency." *J. Chem. Soc. Chem. Commun.*, 1885–1886, 1995.

Allard, et al., "Experimental Study of DOTA–Gadolinium Pharmacokinetics and Pharmacologic Properties", *Investigative Radiology*, 23(1): S271–S274, Sep. 1988.

Arturson, et al., "The Renal Clearance of Dextran of Different Molecular Sizes in Normal Humans." *Scand. J. Clin. Lab. Invest.*, 16: 81–86, 1964.

Blaufox, et al., "Measurement of Effective Renal Plasma Flow in Man By External Counting Method.", *J. Nucl. Med.* 8: 77–85., 1967.

Bornhop, et al., "Fluorescent Tissue Site–Selective Lanthanide Chelate, Tb–PCTMB for Enhanced Imaging of Cancer." *Anal. Chem.* 71: 2607–2615., 1999.

Bousquet, J. "Gd–DOTA: Characterization of a New Paramagnetic Complex." *Radiology*, 166: 693–698., 1988.

Brillet, et al., "Renal Tolerance of Gadolinium—DOTA and Gadolinium– DTPA in Rats", *Investigative Radiology*, 29(3): 352–354, 1994.

Brochner–Mortensen, J., "A Simple Method for the Determination of Glomerular Filtration Rate." *Scand. J. Clin. Lab. Invest.* 30: 271–276, 1974.

Butkus, D., "Persistant High Mortality In Acute Renal Failure. Are We Asking the Right Question?" *Arch. Intern. Med.* 143: 209–212., 1983.

Cacheris, et al., "Thermodynamic Study of Lanthanide Complexes of 1,4,7–Triazacyclononane–N,N',N"–Triacetic Acid and 1,4,7,10–Tetraazacyclododecane–N,N',N", N'"–Tetraacetic Acid", *Inorg Chem.* 26: 958–960, 1987.

Carrie, et al., "Creatinine: An Inadequate Filtration Marker in Glomerular Diseases." *Am. J. Med.* 69: 177–182., 1980.

Chantler, et al., "Estimation of Glomerular Filtration Rate from Plasma Clearance of 51–Chromium Edetic Acid." *Archs. Dis. Child.* 47: 613–617., 1972.

Cohen, et al., "External Monitoring and Plasma Disapperance for the Determination of Renal Function: Comparison of Effective Renal Plasma Flow and Glomerular Filtration Rate." *Pediatrics*, 48: 377–391., 1971.

Costa, et al., "Metal Complexes of Macrocyclic Ligands Containing Pyridine." *Inorg. Chem.* 32: 5257–5265., 1993.

Davidson, et al., "The Use of Fluorescent Probes in Immunochemistry", *Photochemistry and Photobiology*, 52(2): 431–438, 1990.

Desreux, J., "Nuclear Magnetic Resonance Spectroscopy of Lanthanide Complexes with a Tetraacetic Tetraaza Macrocycle. Unusual Configuration Properties." *Inorg. Chem.* 19: 1319–1324, 1980.

Desreux, et al., "NMR Investigation of the Lanthanide Complexes with a 14–Membered Polyaza Polyacetic Macrocycle, TETA. Another Rare Example of Nonlabile Lanthanide Compounds," *Inorg. Chem.* 25: 69–74, 1986.

Horrocks, et al., "Energy Transfer Between Terbium (III) and Cobalt (II) in Thermolysin A New Class of Metal—Metal Distance Probes", *Proc. Nat. Acad. Sci. USA.*, 72(12): 4764–4768, 1975.

(List continued on next page.)

*Primary Examiner*—Michael G. Hartley
(74) *Attorney, Agent, or Firm*—Valarie B. Rosen; Choate, Hall & Stewart

(57) ABSTRACT

A fluorescent agent for monitoring organ function, such as glomerular filtration, renal blood flow, or hepatic function. The agent is injected into a subject and the fluorescence monitored in vivo via time-resolved fluorescent techniques. The agent is a lanthanide ion chelated to a polyaminopolyacetic acid analog. A new clearance agent is also proposed based on a tetraazamacrocycle. Such a clearance agent also finds applications in other fields where fluorescence detection is exploited.

14 Claims, 10 Drawing Sheets

OTHER PUBLICATIONS

Diamandis, E. "Time Resolved Fluorometry in Nucleic Acid Hybridization and Western Blotting Techniques." *Electrophoresis,* 14: 866–875, 1993.

Diamandis, E., "Immunoassays with Time–Resolved Fluorescence Spectroscopy: Principles and Applications," *Clin. Biochem.,* 21: 139–150, 1988.

Dickson, et al., "Time–Resolved Detection of Lanthanide Luminescence for Ultrasensitive Bioanalytical Assays." *J. Photochem. Photobio.B,* 27: 3–19, 1995.

Dickson, et al., "Ultrasensitive Bioanalytical Assays Using Time–Resolved Fluorescence Detection" *Pharmac. Ther.* 66: 207–235, 1995.

Donath, A., "The Simultaneous Determination in Children of Glomerular Filtration Rate and Effective Renal Plasma Flow by the Single Injection Clearance Technique." *Acta. Pediatr. Scand.* 60: 512–527, 1971.

Dorshow, et al., "Noninvasive Fluorescence Detection of Hepatic and Renal Function", *Journal of Biomedical Optics,* 3(3): 340–345, 1998.

Dyckerhoff, et al., "Uber Die Gerinnung Des Blutes." *Biochem. Z.* 288: 271–291., 1936.

Earle, et al., "A Simplified Clinical Procedure for Measurement of Glomerular Filtration Rate and Renal Plasma Flow." *Proc. Soc. Exp. Biol. Med.* 62: 262–264., 1946.

Frisoli, et al., "Pharmacokinetics of a Fluorescent Drug Using Laser–Induced Fluorescence." *Cancer Res.* 53: 5954–5961, 1993.

Geraldes, et al., "Relaxometry, Animal Biodistribution, and Magnetic Resonance Imaging Studies of Some New Gadolinium (III) Macrocyclic Phosphinate and Phosphonate Monoester Complexes", *MRM,* 30: 696–703, 1993.

Hemmila, et al., "Europium as a Label in Time–Resolved Immunofluorometric Assays." *Anal. Biochem.* 137: 335–343, 1984.

Hemmila, I. "Time–Resolved Fluorometric Determination of Terbium In Aqueous Solution," *Anal. Chem.,* 57: 1676–1681., 1985.

Hemmilä, I., Fluoroimmunoassays and Immunofluorometric Assays, *Clin. Chem.* 31(3): 359–370, 1985.

Hilson, et al., "99mTc–DTPA for the Measurement of Glomerular Filtration Rate." *Br. J. Radiol.* 49: 794–799, 1976.

Hosain, et al., "Measurement of Glomerular Filtration Rate Using Chelated Ytterbium–169." *Int. J. Appl. Radiat and Isotopes.,* 20: 517–524, 1969.

Hou, et al., "Hospital–Acquired Renal Insufficiency: A Prospective Study." *Am. J. Med.* 74: 243–248, 1983.

Howanitz, J., "Immunoassay Innovations in Label Technology", *Arch Pathol Lab Med.,* 112: 775–779, 1988.

Hubbard, et al., "Diagnostic Imaging Using Rare–Earth Chelates", *Lasers Med Sci.* 13: 14–21, 1998.

Kellen, et al., "Predictive and Diagnostic Test of Renal Failure: A Review." *Anesth. Analg.* 78: 134–142, 1994.

Kim, et al., "Relaxometry, Luminescence Measurements, Electrophoresis, and Animal Biodistribution of Lanthanide (III) Complexes of Some Polyaza Macrocyclic Acetates Containing Pyridine." *Inorg. Chem.,* 34: 2233–2243., 1995.

Klopper, et al., "Evaluation of 99m Tc–DTPA for the Measurement of Glomerular Filtration Rate." *J. Nucl. Med.* 13: 107–110, 1972.

Leif, et al., "Development of Instrumentation and Fluorochromes for Automated Multiparameter Analysis of Cells", *Clin. Chem.* 23(8): 1492–1498, 1977.

Leung, et al., "Attachment of Fluorescent Metal Chelates to Macromolecules Using "Bifunctional" Chelating Agents", *Biochemical and Biophysical Research Communications,* 75(1): 149–155, 1977.

Li, et al., "Luminescent Polyaminocarboxylate Chelates of Terbium and Europium: The Effect of Chelate Structure", *J. Am. Chem. Soc.* 117: 8132–8138, 1995.

Loncin, et al., "Coordination of Lanthanides by Two Polyamino Polycarboxylic Macrocycles: Formation of Highly Stable Lanthanide Complexes", *Inorg. Chem.* 25: 2646–2648, 1986.

Magerstadt, et al., "Gd(DOTA): An Alternative to Gd(DTPA) as a $T_{1,2}$ Relaxation Agent for NMR Imaging or Spectroscopy", *Magnetic Resonance in Medicine,* 3: 808–812, 1986.

Mathies, et al., "Single–Molecule Fluorescence Detection: A Feasibility Study Using Phycoerythrin". *Applications of Fluorescence in the Biomedical Sciences.* New York: Alan R. Liss, Inc., pp. 129–140, 1986.

Mathis, et al., "Homogeneous Immunoassays Using Rare Earth Cryptates and Time Resolved Fluorescence: Principles and Specific Advantage for Tumor Markers." *Anticancer Res.* 17(14B): 3011–4., 1986. (abstract).

McKinney, et al., "Determination of Purity of Fluorescein Isothiocyanates." *Anal. Biochem,* 7: 74–86., 1964.

Novis, et al., "Association of Pre–Operative Risk Factors with Post–Operative Acute Renal Failure." *Anesth. Analg.* 78: 143–149, 1994.

Perrone, et al., "Utility of Radioisotopic Filtration Markers in Chronic Renal Insufficiency: Simultaneous Comparison of 125I–Iothalamate, 169Yb–DTPA, 99mTc–DTPA and Inulin." *Am. J. Kidney Dis.* 16: 224–235, 1990.

Price, M., "Comparison of Creatinine Clearance to Inulin Clearance in the Determination of Glomerular Filtration Rate." *J. Urol.* 107: 339–340, 1972.

Rabito, et al., "Noinvasive, Real–Time Monitoring of Renal Function: The Ambulatory Renal Monitor." *J. Nucl. Med.* 34: 199–207, 1993.

Rabito, et al., "Renal Function in Patients at Risk of Contrast Material–Induced Acute Renal Failure: Non–Invasive, Real-Time Monitoring." *Radiology,* 186: 851–854, 1993.

Reba, et al., "Indium–113m Diethylene–Tri Aminepentaacetic Acid (DTPA): A New Radiopharmaceutical For Study of Kidneys." *Radiology,* 90: 147–152, 1968.

Richman, et al., "Nitrogen Analogs of Crown Ethers." *J. Am Chem. Soc.* 96: 2268–2270, 1974.

Sapirstein, et al., "Volumes of Distribution and Clearances of Intravenously Injected Creatinine in the Dog.", *Am. J. Physiol.* 181: 330–336, 1955.

Shemesh, et al., "Limitation of Creatinine as a Filtration Marker in Glomerulopathic Patients." *Kidney Int.* 28: 830–838, 1985.

Sigman, et al., "The Measurement of Glomerular Filtration Rate in Man With Sodium Iothalamate 131I(Conray)." *J. Nucl. Med.* 7: 60–68., 1965.

Snyder, et al., "Liver Lipid Response to Intravenous Rare Earths in Rats." *J. Lipid Res.* 1: 125–131, 1959.

Soini, et al., "Fluoroimmunoassay: Present Status and Key Problems." *Clin. Chem.* 25: 353–361, 1979.

Stacy, et al., "Chromium–51 EthylenediaminetetraAcetate for the Estimation of Glomerular Filtration Rate." *Science,* 152: 1076–1078, 1966.

Stettler, et al., "Complex formation with Tetraazacycloalkane—N, $N^I$, $N^{II}$, $N^{III}$—tetraacetic Acids as Function of Ring Size." *Angew. Chem. Int. Ed. Engl.,* 15: 686, 1976.

Taplin, et al., "The Radioactive (I131–Tagged) Rose Bengal Uptake–Excretion Test for Liver Function Using External Gamma–Ray Scintillation Counting Techniques." *J. Lab. Clin. Med.* 45: 665–669, 1955.

Thibault, et al., "Medical Intensive Care: Indications, Interventions and Outcomes." *N. Engl. J. Med.,* 302: 938–942, 1980.

Thomas, et al., "Fluorescence Energy Transfer in the Rapid-Diffusion Limit", *Proc. Natl. Acad. Sci., USA,* 75(12): 5746–5750, 1978.

Walser, et al., "Creatinine Measurements Often Yield False Estimates of Progression in Chronic Renal Failure." *Kidney Int.* 34: 412–418, 1988.

Wedeking, et al., "Comparison of the Biodistribution of $^{153}$Gd–Labeled Gd $(DTPA)^{2-}$, $Gd(DOTA)^-$, and Gd $(Acetate)_n$ in Mice", *Nucl. Med. Biol.* 15(4): 395–402, 1998.

Werko, et al., "The Renal Extraction of Paraaminohipuric Acid and Oxygen in Man During Postural Changes of the Circulation." *Scand. J. Clin. Lab. Invest.* 1: 321–327, 1949.

Yeh, et al., "A New Route to "Bifunctional" Chelating Agents: Conversion of Amino Acids to Analogs of Ethylenedinitrilotetraacetic Acid." *Anal. Biochem.* 100: 152–159, 1979.

\* cited by examiner

FLUORESCENT AGENTS FOR REAL-TIME MEASUREMENT OF ORGAN FUNCTION

This application claims priority from Provisional Application No. 60/219,362, filed Jul. 19, 2000, the contents of which are incorporated herein by reference.

FIELD OF THE INVENTION

This invention pertains to fluorescent agents, instruments, and techniques for measurement of organ function, and, more specifically, for real-time measurement of organ function.

BACKGROUND OF THE INVENTION

Acute renal failure (ARF), as a complication of multiple surgical, medical and obstetrical conditions, represents an important individual and public health problem. Early identification of patients at risk, with prompt elimination of potential insults, is a golden rule that has saved many lives. Unfortunately, despite close implementation of this rule, the disease still accounts for a large morbidity and mortality, with a survival rate of about 50%, a figure which has not substantially improved since 1950 (Butkus, D., *Arch. Intern. Med.*, 143: 209–212, 1983). This poor outcome contrasts with the almost unique ability of the kidney to undergo virtually complete recovery of function following an episode of transient ischemia or toxin-induced cellular destruction. This discrepancy between mortality and the potential for reversibility emphasizes the need for a reconsideration of current diagnostic and therapeutic options with the goal of assuring complete recovery of organ function after an episode of ARF.

Because the clinical condition of patients with ARF is determined largely by prior health status and the nature of the specific insult that led to renal failure, any therapeutic approach used to treat ARF should be simultaneously oriented toward correcting the precipitating cause and the impaired organ function. Hypoperfusion of the kidney is the most frequently recognized single insult leading to ARF in the setting of trauma, surgery, hemorrhage, or dehydration (Kellen, M., S. Aronson, et al., *Anesth. Analg.*, 78: 134–142, 1994; Hou, S., D. Bushinsky, et al., *Am. J. Med.*, 74: 243–248, 1983). Continuous and precise monitoring of cardiopulmonary function in such acute settings has been available for many years and has undoubtedly helped to restore normal circulatory status in the critically ill patient. At the present time, however, monitoring of renal function is done with crude measurements such as urine output and plasma creatinine. Unfortunately, because of their lengthy resolution time (the time required to obtain a single measurement of renal function), none of these parameters can be used for real-time monitoring of renal function. For example, creatinine clearance measurements have a resolution of about 12 hours. By the time a patient's ARF was recognized by this technique, it would be too late to treat the patient and have any hope of saving the kidney. The inadequacy of standard techniques for monitoring renal function during critical care is the most salient limitation for prevention of ARF and for the determination of an appropriate therapy to correct organ failure.

Measurements of glomerular filtration rate (GFR) can be made directly by micropuncture or indirectly by clearance methods. Although direct techniques have produced major contributions in our understanding of the production and regulation of the glomerular ultrafiltrate in laboratory animals, the invasive nature of the procedures renders them of questionable value in humans. Clearance techniques, on the other hand, are normally used to measure renal function in humans. However, because the techniques have such lengthy resolution times, it is quite difficult to detect rapid changes in GFR that may occur under different physiological and pathological conditions. For instance, GFR changes during exercise (Barclay, J., W. Cooke, et al., *J. Physiol.* (*London*), 104: 14, 1946), with orthostatic hypotension (Papper, E. and S. Ngai, *Ann. Rev. Med.*, 7: 213–224, 1956), and with changes in posture (Werko, L., H. Bucht, et al., *Scand. J. Clin. Lab. Invest.*, 1: 321, 1949). The changes in GFR during exercise were only detected when the exercise level was very intense and the changes in cardiopulmonary function were quite persistent (Selkur, E., *Handbook of Physiology: Circulation*, J. Field, Ed. Washington, DC: Am. Physiol. Soc.,. Vol. 2, pp. 1457–1516, 1963). These results suggested that changes in GFR at low levels of exercise may have gone undetected due to the poor resolution time of the clearance techniques. In order to fully understand this important limitation of clearance techniques, one should ask how fast the changes in GFR might occur under an ideal experimental condition emulating a hypoperfusion event of the kidney. Studies performed in the isolated, perfused dog kidney indicate that sudden changes (within seconds) in perfusion pressure are very closely followed (also within a few seconds) by changes in GFR (Harvey, R., *Circulation Res.*, 15: 178–182, 1964). Clearance techniques, on the other hand, have a totally different resolution time. It was recognized very early that a considerable interval (more than 30 minutes) is required for a sudden change in GFR to be initially detected in the composition of urine (Smith, H., *The Kidney: Structure and Function in Health and Disease*, New York: Oxford University Press, 1951). This time most likely represents the time required for the ultrafiltrate to pass down the tubules, collecting ducts, and ureters before it reaches and equilibrates with the urine already contained in the urinary bladder. Since at least two samples are needed to determine that the measurement is done at equilibrium, the minimal ideal resolution time for this procedure will be about 1 hour. This, plus the usual delay in measuring the concentration of an agent in urine and blood samples, represents a significant limitation in the use of this procedure for bedside, real-time, monitoring of renal function in patients with ARF.

Renal function has traditionally been measured by creatinine clearance. It is now recognized, however, that in addition to the technical problems with creatinine measurement and with urine collection, creatinine clearance is not an accurate measure of GFR (Carrie, B., H. Golbertz, et al., *Am. J. Med.*, 69: 177–182, 1980; Price, M., *J. Urol.*, 107: 339–340, 1972). Quantitative methods for measuring renal glomerular and tubular function with clearance techniques have been available for many years. The nonendogenously produced substance inulin probably meets the requirements of an ideal GFR agent (Smith, 1951). Although it has remained the "gold standard", the chemical methods of measurement are unfortunately too cumbersome for routine use. In addition to seeking a substance that fulfills the requirements of a GFR agent, researchers have also sought to overcome the other major source of error in clearance measurements, namely, incomplete urine collection. Two approaches have been found to be successful. The most accurate, but technically difficult, is the constant infusion of a substance until an equilibrium is reached, at which point the plasma level is steady. The rate of infusion is then equal to the rate of loss in the urine and no urine collection is necessary (Earle, D. and R. Berliner, *Proc. Soc. Exp. Biol.*

Med., 62: 262–264, 1946). Alternatively, the rate of plasma disappearance of a substance after a single intravenous injection is determined, enabling calculation of GFR (Sapirstein, L., D. Vidt, et al.,*Am. J. Physiol.*, 181: 330–336, 1955; Chantler, C. and T. Barratt, *Archs. Dis. Child.*, 47: 613–617, 1972). The disappearance of the tracer is determined by taking multiple blood samples over a period of 3 to 4 hours and then measuring the radioactivity of the samples. In addition to the requirements that a GFR agent must be freely filtered by the glomerulus, four other basic criteria must apply if a substance is to be used to measure clearance without urine collection:

a. it must not be metabolized;
b. it must be cleared exclusively by glomerular filtration (no other route of excretion other than renal);
c. it must not be bound to plasma protein or extracellular components; and
d. it must not be reabsorbed by the nephron. $^{51}$Cr-EDTA, $^{99m}$Tc-DTPA, and $^{125}$I-sodium iothalamate meet these requirements and are the accepted choices for measuring GFR in most clinical studies (Chantler, 1972; Sigman, E., C. Ellwood, et al.,*J. Nucl. Med.*, 7: 60–68, 1965). Most of these clearance techniques, although more accurate than creatinine clearance, have not been widely used because of their technical complexities. Moreover, all of these methods are grossly inadequate for real-time and accurate monitoring of renal function. Clearly, a method for real-time, accurate, and continuous measurement of GFR in acute clinical settings will be a tremendous help in the management of patients who have ARF or are at risk of developing ARF.

Because glomerular filtration is the first step in urine production, the measurement of GFR represents the most convenient and reliable parameter for evaluation of renal function. Although there is general agreement that inulin clearance is the best measure of GFR, there are, as indicated above, several inherent difficulties in the use of this agent. As an alternative to inulin, a number of agents labeled with radioactive tracers have been introduced in the past few years for the measurement of GFR, including several chelates such as $^{51}$Cr-EDTA (Stacy, B. and G. Thorburn, *Science*, 152: 1076–1078, 1966), $^{111m}$In-DTPA (Reba, R., F. Hosain, et al., *Radiology*, 90: 147–152, 1968), $^{169}$Yb-DTPA (Hosain, F., R. Reba, et al., *Int. J. AppL Radiat.*, 20: 517–524, 1969; Perrone, R., T. Stainman, et al., *Am. J. Kidney Dis.*, 16: 224–235, 1990) and $^{140}$La-DTPA (Bianchi, C. and M. Blaufox,*J. Nucl. Biol. Med.*, 12: 117–122, 1968). The introduction of a kit for rapid and simple preparation of $^{99m}$Tc-DTPA has made this the most readily available agent used to measure GFR, either by blood clearance (Klopper, J., W. Hauser, et al.,*J. Nucl. Med.*, 13: 107–110, 1972; Barbour, G., C. Crumb, et al., *J. Nucl. Med.*, 17: 317–320, 1976; Hilson, A., R. Mistry, et al., *Br. J. Radiol*, 49: 794–799, 1976) or by external detection (Blaufox, M., E. Potchen, et al.,*J. Nucl. Med.*, 8: 77–85, 1967; Cohen, M., J. Patel, et al., *Pediatrics*, 48: 377–391, 1971; Thirimurthi, K., M. Casey, et al., *Nucl. Med. All. Sci.*, 28: 245–250, 1984).

Real-time monitoring of renal function: Taking advantage of this opportunity, we developed a new approach for noninvasive and real-time monitoring of renal function (Rabito, C., R. Moore, et al., *J. Nucl. Med.*, 34: 199–207, 1993). The method is based on a variation of the single-injection technique (Donath, A., *Acta. Pediatr. Scan.*, 60: 512–527, 1971), in which continuous and instantaneous measurement of radioactivity is performed with an external detector rather than with the intermittent and deferred assay of venous blood and is described more fully in our commonly owned patents, U.S. Pat. Nos. 5,647,363 and 5,301,673, the contents of which are incorporated herein by reference. A radiation detector attached to a miniature data logger was used to monitor the clearance of $^{99m}$Tc-diethylene triamine pentaacetic acid ($^{99m}$Tc-DTPA) from the extracellular space (Rabito, 1993). After a short equilibration period, the system behaved as a compartment system with first order kinetics. In this system, the log of activity varies linerally with time, with the rate constant given by the slope of the resulting line. Two important assumptions are involved in the use of this approach for monitoring renal function. The first assumption is that the measurement of the rate constant can be performed fast enough to approach real-time conditions. For instance, the slope or rate constant can be calculated from several consecutive measurements of activity performed for a few seconds during a short interval of only a few minutes. This rate constant can be updated every minute or less after entering each new individual measurement. The second assumption is that the measurement of the rate constant for the clearance of an "ideal" glomerular filtration agent from the extracellular space constitutes a precise and reproducible estimate of GFR. In the single injection technique, GFR is usually calculated as the volume of distribution of the GFR agent multiplied by the rate constant. However, because the volume distribution is assumed to be constant after normalization by body surface area, the rate constant per se represents an accurate estimate of GFR. These assumptions are supported by the excellent correlation between the rate constant for clearance of $^{99m}$Tc-DTPA and simultaneous GFR measurements performed with a standard $^{125}$I-iothalamate clearance technique in 50 patients with different degrees of renal dysfunction (FIG. 1).

Because of their limited resolution time, none of the current techniques to measure renal function could be used to demonstrate the improvement in the resolution time of this novel approach. As an alternative, we studied the response-time of the technique by using the device in patients undergoing a medical procedure with high incidence of ARF. The rationale was that, in the case of ARF, the instrument should closely follow any rapid change in the renal function that may take place during the event. Validation, however, could be performed by comparison with a standard clearance technique before and after the intervention and once the renal function has become stable. The procedure was used, for instance, to monitor renal function in patients at risk for ARF in the intensive care unit or during angiography. The results demonstrated that the technique detected rapid changes in renal function with a resolution time of as little as 2.5 to 5 min. (Rabito, 1993; Rabito, C., F. Panico, et al., *J. Am. Soc. Nephrol.*, 4: 1421–1428, 1994; Rabito, C., L. Fang, et al., *Radiology*, 186: 851–854, 1993).

Although highly innovative, this technique has some limitations. First, due to strict regulations and high costs, not every physician or medical institution has access to the use of radioactive tracer techniques. Second, due to the risk of radiation exposure, the technique cannot be used to measure renal function during surgery, or in infants and pregnant or postpartum women. To overcome these limitations, we propose in this invention the development of fluorescent GFR and renal blood flow (RBF) agent to be used in conjunction with a fluorescence-activated renal monitor, to thereby eliminate the limitations of the current radioactive GFR and RBF agents.

SUMMARY OF THE INVENTION

It is an object of this invention to provide fluorescent agents to monitor specific functions in specific organs.

It is also an object of this invention to provide an instrument for standard and time-resolved transcutaneous fluorescence measurements of these agents.

It is a further object of this invention to provide a method for real-time measurement and monitoring of organ function determined from transcutaneous fluorescence measurements of these agents.

In one aspect, the invention is a method of detecting a clearance function in a subject. The method comprises providing an electroluminescent agent in a circulatory system of the subject, irradiating a tissue site with electromagnetic radiation having sufficient energy and intensity to be absorbed by the agent, detecting the intensity of emission from the tissue site, and repeating the step of detecting at known time intervals. The agent is not metabolized by the subject and is only cleared by a single mechanism. In addition, the agent does not bind plasma, protein, or extracellular components and is not reabsorbed by the subject. The method may further comprise irradiating the tissue site with a laser, for example, a pulsed laser. The step of repeating may be performed until elapsed time since the step of irradiating is about 90% of the decay time, for example, 50 ns or greater. After the step of detecting has been repeated a predetermined number of times, the step of irradiating may be repeated, and a background emission may have decayed to an insignificant level before the step of detecting is performed.

In one embodiment, the agent may be cleared exclusively by the glomerulus and may comprise a polyaminopolyacetic acid derivative conjugated with an electroluminescent moiety, which may comprise a lanthanide ion. The lanthanide ion may be trivalent and may comprise $Ce^{+++}$, $Nd^{+++}$, $Sm^{+++}$, $Eu^{+++}$, or $Tb^{+++}$. The conjugate may exhibit fluorescence when irradiated with red or infrared light.

The polyaminopolyacetic acid derivative may be selected from diethylenetriaminepentaacetic acid (DTPA) ethylene glycol N,N,N',N'-tetraacetic acid (EGTA), or polyaminopolybis(2-aminoethyl ether) acetic acid. The polyaminopolyacetic acid derivative may comprise

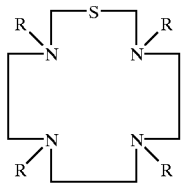

S may be a cyclic organic moiety having at least one oxygen or nitrogen atom, and R may be an organic functionality, for example, an acetate or a p-toluene sulfonyl group. S may be aromatic, aliphatic, substituted, or unsubstituted. For example, S may comprise a furanyl, tetrahydrofuranyl, pyrrolidinyl, furoyl, pyrrolyl, or substituted derivatives of these. Exemplary substituents include $NO_2$, $NH_2$, isothiocyanato, semicarbazido, thiosemicarbazido, maleimido, bromoacetomido, and carboxyl groups.

In another aspect, the invention is an apparatus for detection of a clearance rate of a substance from extracellular fluid. The apparatus comprises a light source capable of producing light having sufficient intensity and energy to be absorbed by an electroluminescent moiety in the subject's extracellular fluid, an optical fiber to deliver light from the light source to the subject, a detector, an optical fiber to deliver light emitted by the electroluminescent moiety to the detector, and processing means to calculate the rate of depletion of the electroluminescent moiety based on values measured by the detector. The light source may be a pulsed laser having a frequency such that it emits light at a time interval which is a predetermined fraction of a decay time of the electroluminescent moiety.

In another aspect, the invention is an electroluminescent molecule. The molecule comprises a polyaminopolyacetic acid derivative conjugated with an electroluminescent moiety and exhibits fluorescence when irradiated with red or infrared light. The molecule may be attached to an antibody, a DNA fragment, an RNA fragment, an enzyme, or an enzyme co-factor attached to the polyaminopolyacetic acid derivative. The molecule may also include an oligonucleotide. In another embodiment, the invention is a method of performing magnetic resonance imaging on a patient. The method comprises injecting the electroluminescent molecule into a patient, exposing the patient to a magnetic field, exposing the patient to a radio frequency pulse, and measuring the emission of hydrogen ions within the patient after removal of the pulse.

In another aspect, the invention is a method of performing immunochemical analysis. The method comprises associating a first electroluminescent complex with an analyte, exposing the first electroluminescent complex to light at an absorbance wavelength of the complex, and detecting light emitted by the first electroluminescent complex. The first complex comprises a bicyclic polyaminopolyacetic acid analog and an electroluminescent agent chelated to the bicyclic polyaminopolyacetic acid analog. The electroluminescent agent may comprise a lanthanide ion. The lanthanide ion may be trivalent and may comprise $Ce^{+++}$, $Nd^{+++}$, $Sm^{+++}$, $Eu^{+++}$, or $Tb^{+++}$. The method may further comprise associating a second ligand labeled with a second electroluminescent complex with a second analyte, wherein the emission wavelength of the second complex is detectably different from the emission wavelength of the first complex. The method may be performed with more than two ligands and complexes. The electroluminescent complex may exhibit a decay time greater than 50 ns. The steps of exposing and detecting may be repeated. The method may further comprise attaching a first ligand to the analyte, wherein the first electroluminescent complex is associated with the analyte via attachment to the ligand; alternatively, the first electroluminescent complex may be attached to the first ligand via a second ligand. The analyte may be immobilized on a support, for example, via a ligand. Association may comprise removing an electroluminescent agent associated with the analyte and coordinating the electroluminescent agent with the bicyclic polyaminopolyacetic acid analog to form the first electroluminescent complex. In this embodiment, the bicyclic polyaminopolyacetic acid analog is not attached to the analyte, and the electroluminescent agent is attached to the analyte via a ligand. The bicyclic polyaminopolyacetic acid analog may be sequestered in a micelle. The ligand may comprise an antibody, a DNA fragment, an RNA fragment, an enzyme, or an enzyme co-factor. The polyaminopolyacetic acid derivative may comprise

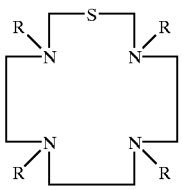

S may be a cyclic organic moiety having at least one oxygen or nitrogen atom, and R may be an organic functionality, for example, an acetate or a p-toluene sulfonyl group. S may be aromatic, aliphatic, substituted, or unsubstituted. For example, S may comprise a furanyl, tetrahydrofuranyl, pyrrolidinyl, furoyl, pyrrolyl, or substituted derivatives of these. Exemplary substituents include $NO_2$, $NH_2$, isothiocyanato, semicarbazido, thiosemicarbazido, maleimido, bromoacetomido, and carboxyl groups.

In another aspect, the invention is a molecule comprising

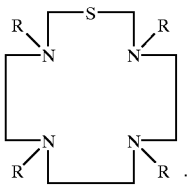

S may be a cyclic organic moiety having at least one oxygen or nitrogen atom, and R may be an organic functionality, for example, an acetate or a p-toluene sulfonyl group. S may be aromatic, aliphatic, substituted, or unsubstituted. For example, S may comprise a furanyl, tetrahydrofuranyl, pyrrolidinyl, furoyl, pyrrolyl, or substituted derivatives of these. Exemplary substituents include $NO_2$, $NH_2$, isothiocyanato, semicarbazido, thiosemicarbazido, maleimido, bromoacetomido, and carboxyl groups.

BRIEF DESCRIPTION OF THE DRAWING

The invention is described with reference to the several figures of the drawing, in which.

DETAILED DESCRIPTION

The present invention provides laser fluorescent dye derivatives and lanthanide chelates for real-time, transcutaneous fluorescence measurements of organ function, for example, glomerular filtration rate, renal blood flow, and hepatic function. To be considered suitable, the new fluorescent agent should have several additional characteristics besides the requirements described above. First, for optimal tissue penetration and minimal background interference, the excitation wavelength of a new agent should be greater than 600 nm. Preferably, the emission wavelength will be in the red or infrared to maximize tissue penetration. Second, the new agent should be very soluble and stable in aqueous solutions. Third, the agent should be non-toxic.

Figure 1:
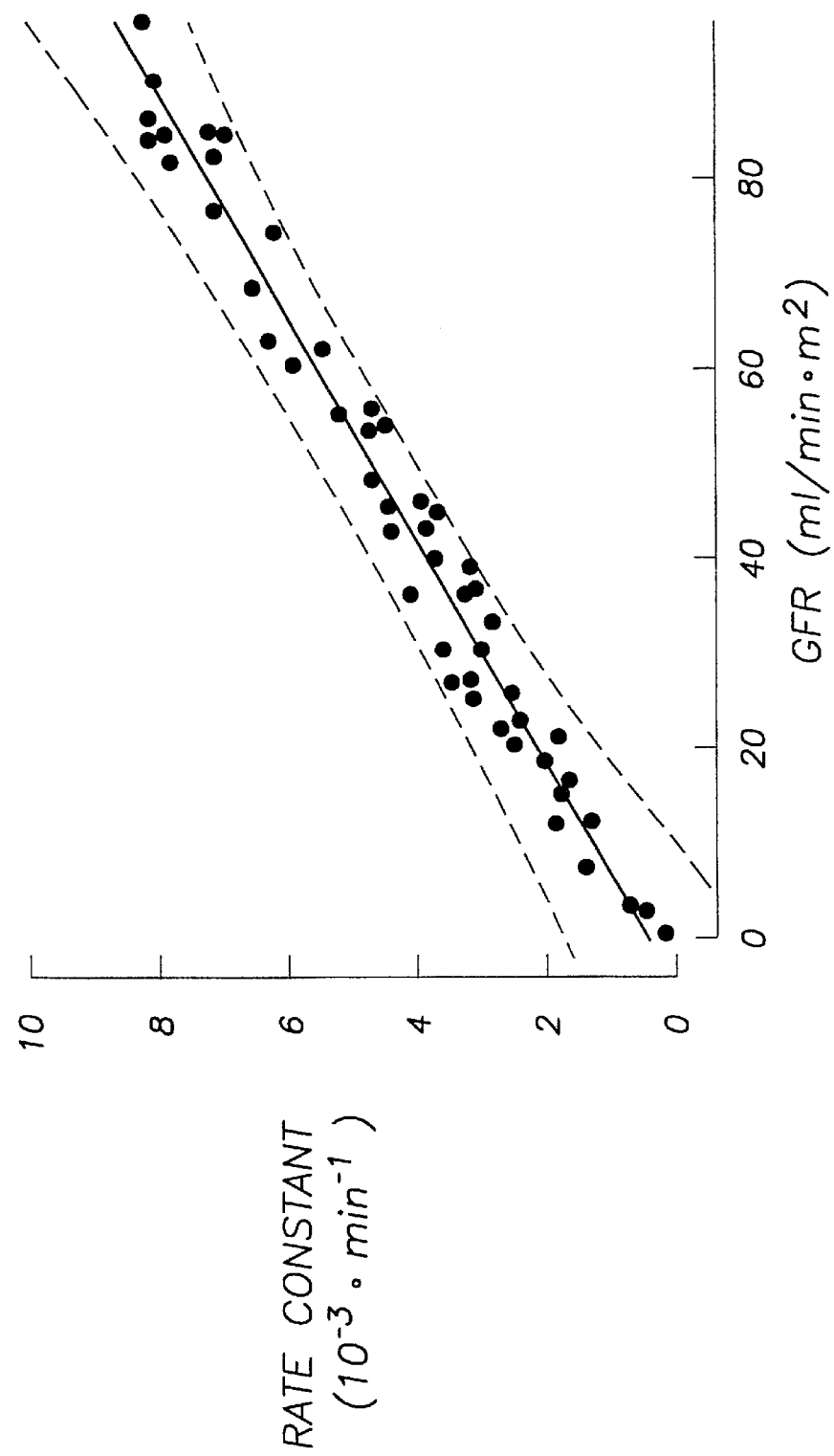
FIG. 1 is a graph correlating the rate constant for clearance of $^{99m}$Tc-DTPA and measured glomerular filtration rate (broken line: 95% confidence limit; n=50)
Figure 2:
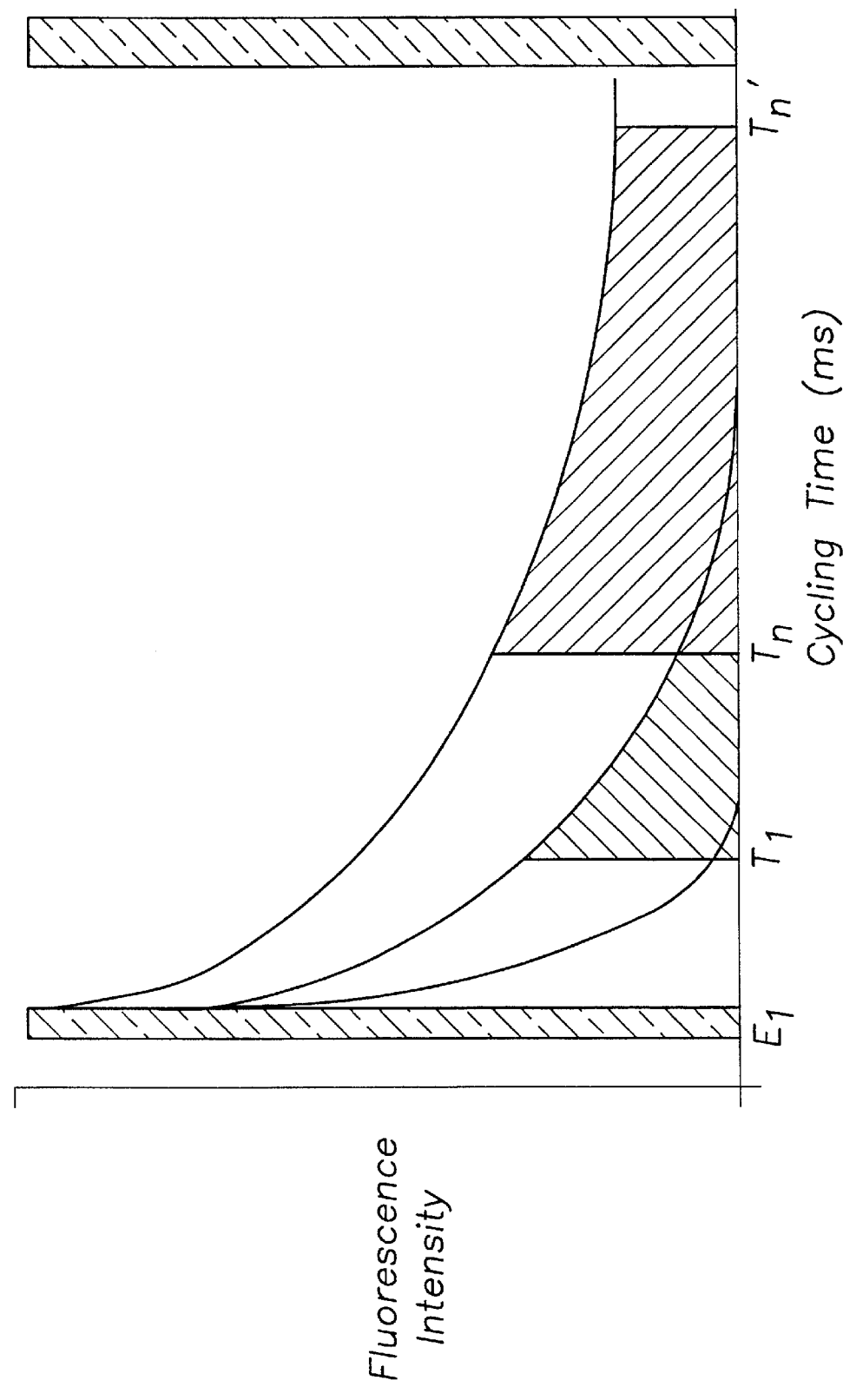
FIG. 2 is a graph illustrating the principle of time-delayed fluorometry.

In comparison with the radioisotope method, the intrinsic sensitivity of fluorometric assay is extremely high (Mathies, R. and L. Stryer, *Applications Of Fluorescence In The Biomedical Sciences*, Taylor D. L., Murphy R. F., Canni F., Birge R. R., Eds. New York: Alan R. Liss, Inc., pp. 129–140, 1986). Unfortunately, the high sensitivity obtained in thoroughly in vitro controlled conditions is lost in less optimal in vivo surroundings as a result of background interference (Soini, E. and I. Hemmila, *Clin. Chem.*, 25: 353–361, 1979). However, the intrinsic sensitivity of the fluorometric analysis should be restored in vivo by taking advantage of both the temporal and spectral resolutions of the technique, recommending fluorometry as a method for real-time renal monitoring without the disadvantages of radiotracers. The background level in fluorometric analysis is a sum of several factors, including scattering and the presence of other fluorescent compounds. Scattering from solvents, solutes, and particles results in background fluorescence in fluorometric measurements, especially when measuring fluorescent probes of short Stokes shift. In addition to scattering, sample constituents like protein, hemin, NADH, etc., cause background fluorescence extending from 300 nm to nearly 600 nm (Soini, 1979). Another important characteristic of this background fluorescence is that its average decay time is less than 50 ns (Mathies, 1986). Two different approaches can be used to reduce or eliminate background activity in the in vivo measurements. One is, as proposed before, to select fluorescent agents with an emission wavelength higher than 600 nm. The other is to use time-resolved fluorometry. Time-resolved fluorometry is a method by which the fluorescence emission is counted after a certain delay time following pulse excitation (Soini, 1979). With this system, background fluorescence can be eliminated, provided that the decay time of the specific signal is substantially longer than the average decay of the background (FIG. 2). FIG. 2 shows that after a pulse excitation A, the background radiation B decays rapidly, allowing detection of emission from Tb (C) and Eu (D), before a subsequent excitation A. If the decay time is long enough, several measurements can be made following excitation at time $E_1$ before the fluorophore must be re-excited. As shown in FIG. 2, once the background fluorescence decays sufficiently ($T_1$), measurements can be repeated between times $T_1$ and Tn or Tn', following which the fluorophore is re-excited. In addition, this technique also prevents quenching, a process in which fluorophores stop emitting when they are excited too long or too often. Time-resolved fluorometry enables both excitation times and frequencies to be reduced, enabling longer intervals during which renal function may be measured.

Figure 9:
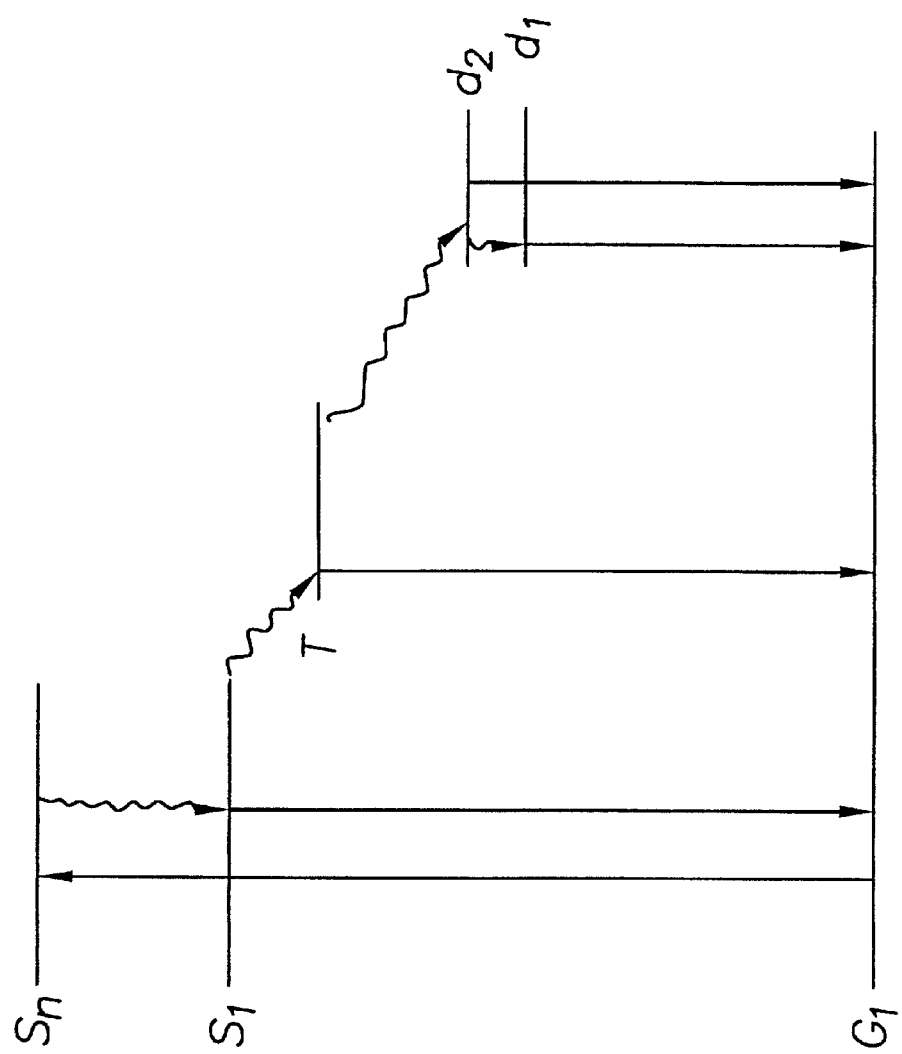
FIG. 9 illustrates the excitation and decay processes resulting in the advantageous emission properties of lanthanide atoms.

The utility of lanthanide chelates for time-delayed fluorometry stems from the unique luminescence properties of these complexes. While the luminescence of these molecules is commonly described as fluorescence, the relaxation mechanism of the excited atom is actually much more complex. As shown in FIG. 9, when a lanthanide chelate is irradiated, the ligand molecule absorbs enough energy to be excited to state $S_n$. The ligand quickly relaxes to singlet excited state $S_1$, a non-radiative process. Relaxation from this state to ground state G is properly termed fluorescence; however, the resulting emission would not be useful for time-resolved techniques. The ligand may also relax from the singlet state $S_1$ to triplet state T via a non-radiative mechanism. Relaxation via emission from this state is called phosphorescence. This emission is relatively slow (on the order of milliseconds) in comparison to fluorescence (on the order of nanoseconds). However, if the energy is transferred to the metal ion (states $d_1$ or $d_2$); then the complex may relax to the ground state either directly from $d_1$ or $d_2$ or indirectly after relaxation from $d_2$ to $d_1$. As can be seen in FIG. 9, the emission wavelength for this process is much different than for the absorption wavelength. In addition, relaxation from state $d_2$ or $d_1$ is even slower than relaxation from the state T. Indeed, the fluorescence lifetime of a conventional fluorophore rarely exceeds 100 ns; the fluorescence lifetime of a lanthanide ion ranges between 100 $\mu$s and 1000 $\mu$s (Diamandis, E. P., *Electrophoresis*, 14: 866–875, 1993). The slow emission and large energy (and emission wavelength) difference between $S_1$ and either $d_2$ or $d_1$ make time-resolved fluorometry a very powerful technique. The slow emission also facilitates real-time monitoring by maximizing the intervals during which measurements may be made and reducing the interruptions due to re-excitation of the fluorophore.

Figure 3:
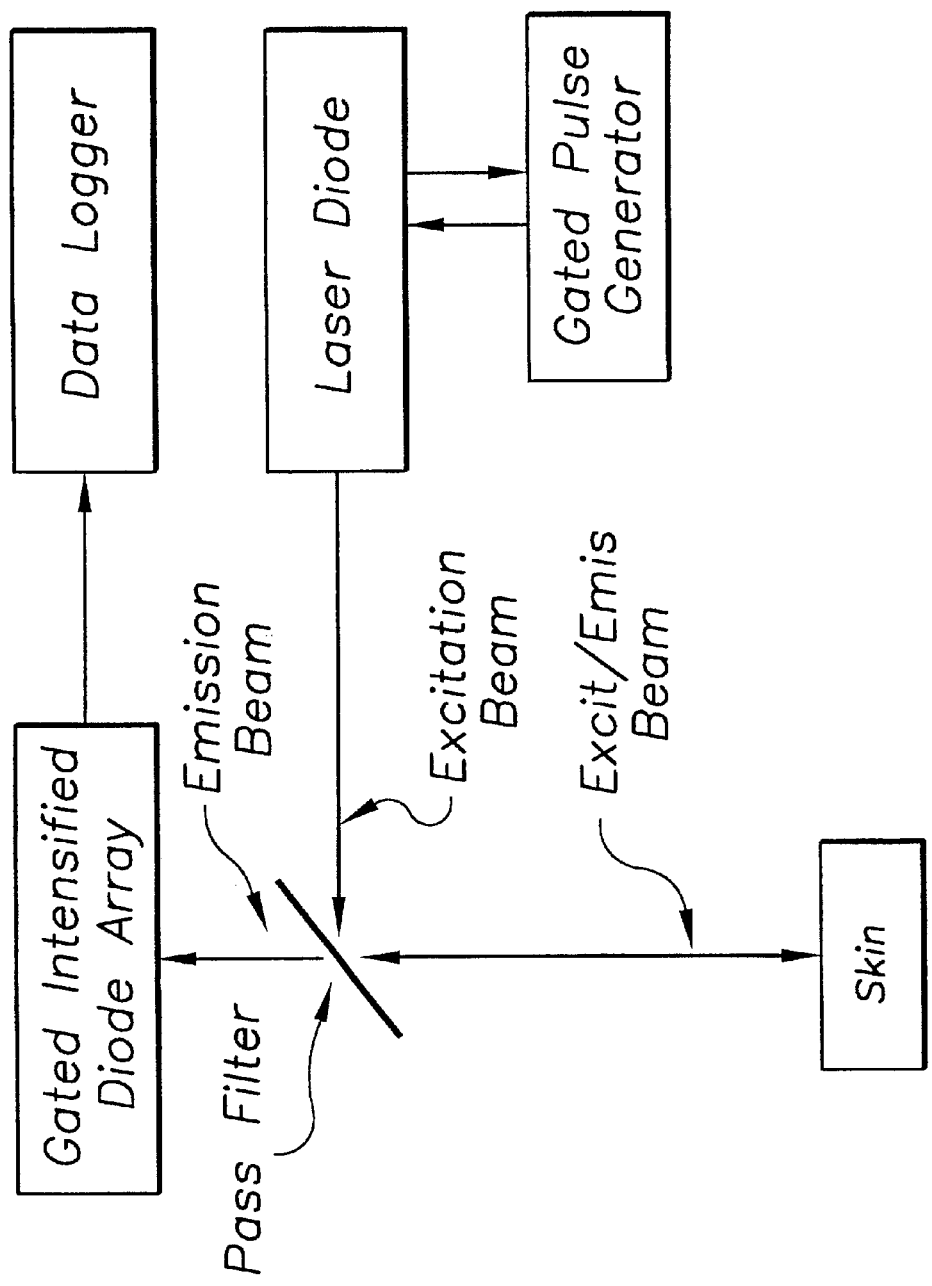
FIG. 3 is a schematic of a laser-induced fluorescence instrument for use with the invention.

Feasibility Study: Before pursuing the rather complex and time consuming process that represents the synthesis and screening for a suitable fluorescent GFR agent, the feasibility of using transcutaneous fluorescence measurements (TFM) to measure the tissue concentration of the fluorescent agent was determined. The study was performed with a laser induced fluorescence system (Frisoli, J., E. Tudor, et al., *Cancer Res.*, 53: 5854–5961, 1993). A basic layout of the system is shown in FIG. 3. A pulse-nitrogen laser (DLM VSL-337ND; Laser Science Inc. Cambridge, Mass.) was used to pump a Dye Laser 220 (Laser Science, Inc.) containing rhodamine 610 dye (Exciton Chemical Co., Dayton, Ohio.). The 610 nm excitation pulses were launched into a 600 nm core diameter fused silica optical fiber (Superguide-G; Fiberguide Industries, Stirling, N.J.) with a 5 mm focal length. After coupling, reflection, and fiber losses, the typical pulse energy incident on the tissue was approximately 10 $\mu$J. Fluorescence from the tissue was collected by a second 600 $\mu$m fiber and separated by a constant distance (one fiber diameter plus cladding and jacket=800 $\mu$m). The output of the collection fiber was optically coupled to a quartz fiber bundle having a circular arrangement of fibers at the input. The fibers at the output end of this bundle were arranged linearly and served as a 0.1 mm×2.5 mm entrance slit for a f/3.8, 0.275 m polychromator (Monospect 27; Anaspect, Acton, Mass.). A long pass filter (CS 2–59; Swift Glass Co., Elmira, N.Y.) was inserted before the quartz fiber bundle to eliminate scattered light. Fluorescence for wavelengths between 300 and 800 nm was recorded using an intensified 1024-diode array controlled by an optical multichannel analyzer (OMA III; Princeton Applied Research, Princeton, N.J.). The intensifier was gated with 100 ns pulses centered on the 3 ns laser pulse. A complete spectrum was recorded with each excitation pulse, and 50 spectra were averaged for each measurement. Although rather bulky, this laser-induced fluorescence (LIF) system has a versatility that is essential for the selection of the most appropriate excitation beam, optic filters, and detector system for the final design of FARM.

Drug uptake and clearance measurements were performed in 75–100 g male Syrian hamsters (Charles River Laboratories, Wilmington, Mass.) after the intravenous injection of 10 mg/kg body weight of chloroaluminum sulfonate phthalocyanine (CASPc). The fluorescence measurements were performed after the hamsters were made temporarily unconscious by immersion in a $CO_2$ atmosphere. The optical fibers were placed in gentle contact with the tissue (tongue) and a spectrum was acquired as described before. The fluorescence intensity at 684 nm was monitored as a function of time after injection of the dye. Some autofluorescence was excited by 610 nm light, but interference was minimal at 684 nm and was eliminated by subtracting the preinjection signal intensity for each hamster from all subsequent spectra. Absolute CASPc concentrations in the tissue were determined by alkaline chemical extraction in experiments utilizing a separate group of hamsters. The absolute amount of CASPc was determined by measuring the fluorescence spectrum of the supernatant in a 2 mm thick cuvette using the LIF instrument. Data were analyzed with a multicompartment pharmacokinetic model. The results showed that there was a positive linear correlation between the LIF intensity and CASPc concentration as determined after extraction of the dye. Moreover, the changes in CASPc concentration (obtained from the TFM) versus time followed the changes in CASPc tissue concentration very closely, as determined after extraction of the dye. These results demonstrate that is highly possible to determine changes in the tissue concentration of a fluorescent agent by measuring the transcutaneous fluorescent signal from this agent and that there is no significant interference from the different tissue components in this type of measurement. Moreover, these results demonstrate the utility of fluorescent techniques for real-time monitoring of renal function. Although CASPc is not a GFR agent, the dye was used as a temporary alternative to demonstrate the feasibility of using the transcutaneous fluorescence measurements to measure the tissue concentration of the fluorescent dye before pursuing the synthesis of the appropriate fluorescent GFR agent.

Fluorescent Agents: Two different procedures were used to obtain the new fluorescent agents. Both approaches employed an agent with clearance characteristics of an "ideal" GFR agent (for instance EDTA, DTPA, low molecular weight Dextran, or a polyazamacrocyclic molecule) as the primary reactant. Selecting a stable GFR agent as the basic starting reactant increases the likelihood that the final fluorescent product will retain most, if not all of the properties of the initial GFR agent. In one of the procedures, the fluorescence marker was a laser dye with a long emission wavelength, e.g. nile blue, oxazine 750, or indocyanine green, and, in the other, a trivalent lanthanide such as neodymium.

Figure 4:
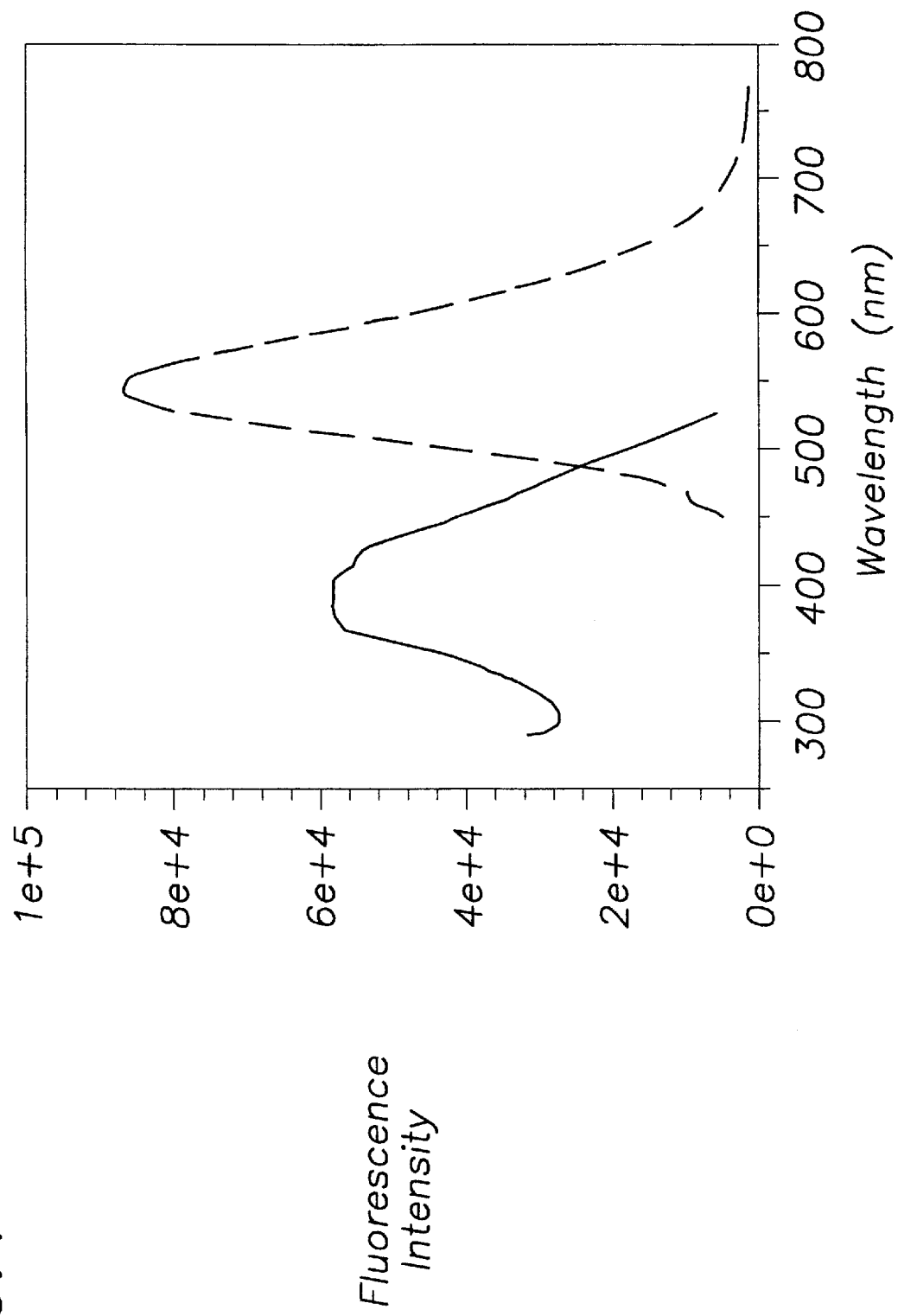
FIG. 4 is a graph showing the fluorescence excitation (continuous line) and emission (broken line) spectra of nile blue-DTPA.

For the synthesis of a nile blue-DTPA conjugate, 0.1 g of DTPA dianhydride (ccDPTA) was dissolved in 6 ml of dimethyl sulfoxide (DMSO) in a round bottom flask. Ninety mg of nile blue were dissolved in DMSO and 36 $\mu$L of triethyl amine were added, turning the solution purple. The nile blue solution was added drop wise to the solution of ccDTPA while stirring. The solution turned blue. Thirty-eight $\mu$L of triethanolamine (TEA) were added to the final mixture, turning the solution purple. After mixing, the mixture was heated to 60° C. and stirred for 2 hours. The reaction mixture was then loaded onto a silica gel column and eluted with acetone:ethylacetate. The fractions corresponding to the nile blue-DTPA conjugate were pooled and evaporated, yielding a magenta colored oil. The oil was rechromatographed on a second silica gel column using acetone as eluant. The nile blue-DTPA conjugated fractions were pooled and rotate-evaporated to give a magenta colored oil. Silica thin layer chromatography (TLC) using ethylacetate:ethanol:TEA (40:40:1) indicated that the nile blue-DTPA conjugate migrated as a single spot with an Rf of 0.9 while the nile blue dye migrated with an Rf of 0.5. Fluorometric analysis (FIG. 4) indicated that the coupling of DTPA to the 5-amino group of nile blue produced a shift in the emission fluorescence from 695 nm to 530 nm, while the maximal excitation remained virtually unchanged at approximately 390 nm. The shift in emission wavelength results in a excessively small Stokes shift ($\lambda_{emission}-\lambda_{excitation}$) for the conjugate. Because of the overlap between the excitation and emission spectra, it is difficult to distinguish the two in real-time measurements. On the other hand, while lanthanide chelates can be produced using similar methods, the emission wavelength of the product is not significantly reduced in comparison with that of the free ion.

Because none of the laser dyes discussed above have sufficiently long decay times for use in time-delayed fluorometry, lanthanide chelates were also investigated. They are known to have a long decay-time for fluorescence, making them an optimal choice for time-resolved techniques. Trivalent lanthanide ions like $Ce^{3+}$, $Nd^{3+}$, $Sm^{3+}$, $Eu^{3+}$, and $Tb^{3+}$ exhibit a special kind of fluorescence characterized by narrow-banded emission lines and long fluorescence decay times. One of the limitations of lanthanide ions, however, is that alone they produce a very weak fluorescence signal. To improve the fluorescence signal, the lanthanide ions need to be combined with an appropriate enhancer. When chelated with suitable light absorbing ligands, the ion fluorescence is enhanced by several orders of magnitude.

The best known and most widely used ligands to produce fluorescent lanthanide chelates are the β-diketones, especially their fluorinated aromatic forms (Hemmila, I., S. Dakubu, et al., *Anal Biochem.*, 137: 335–343, 1984; Hemmila, I., *Anal Chem.*, 57: 1676–1681, 1985). Although europium could be measured with high sensitivity as a β-diketone chelate, this approach has important limitations. First, since the fluorescent GFR agent is distributed in a aqueous media (extracellular space), the β-diketone has to be solubilized with the use of a nonionic detergent (Hemmila, 1984). Second, the binding of the chelate's components is not strong enough to avoid spontaneous dissolution in water (Hemmila, 1984) and, as a result, loss of fluorescence and expression of possible toxic effects of the lanthanide and β-diketone. All of these limitations can be circumvented by the use of an enhancer with strong chelating properties from which the lanthanide will dissociate very slowly, or not at all, under the required experimental conditions.

Figure 5:
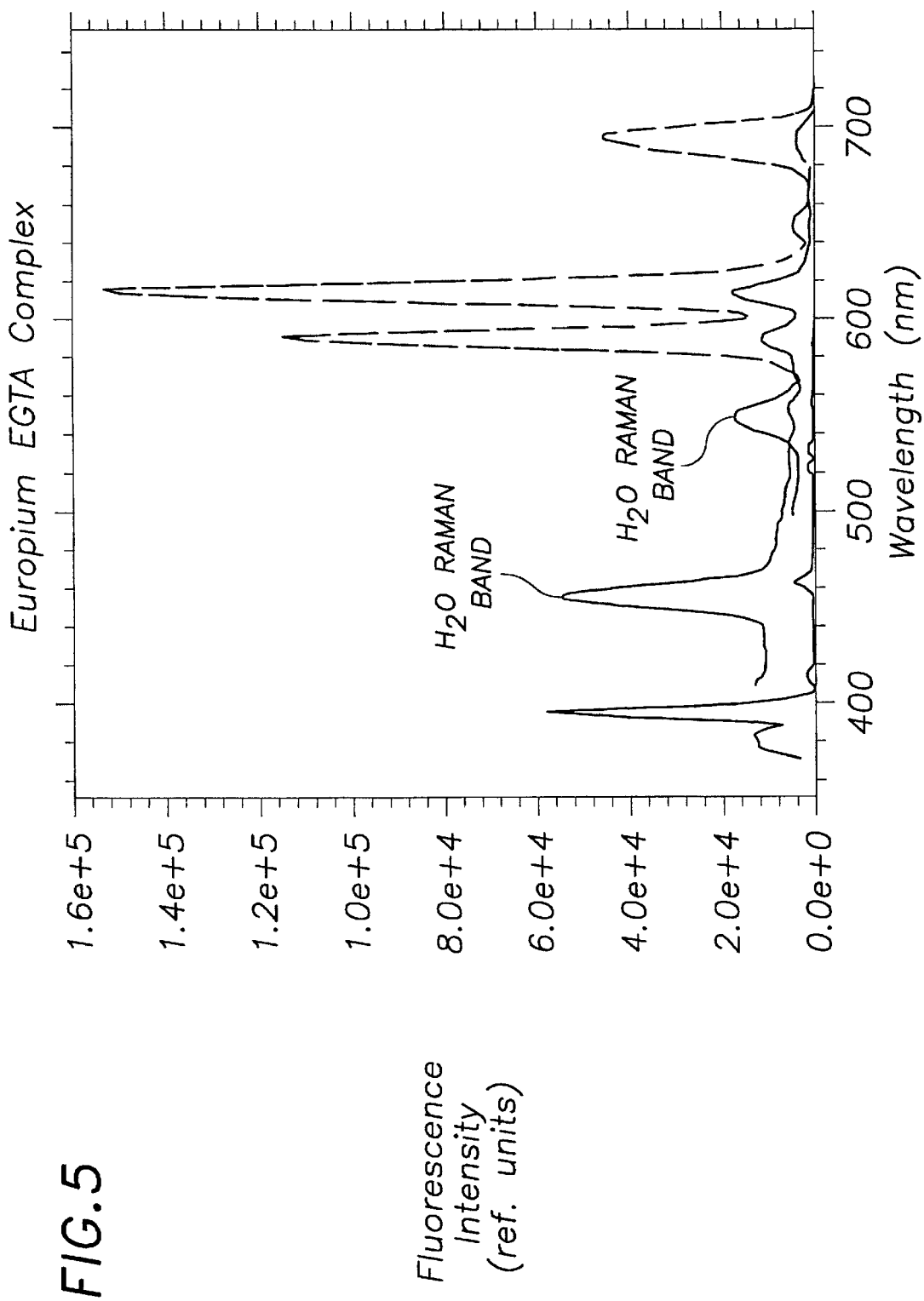
FIG. 5 is a graph showing the fluorescence excitation (continuous line) and emission (broken line) spectra of Eu-EGTA.

The only group of chelating agents known to produce highly soluble and stable lanthanide chelates are the polyamino polyacetic acid analogs. Although previous studies have shown that the chelate between the most commonly used members of this group (EDTA) and europium is essentially non-fluorescent (Hemmila, 1984), the fluorescence of the chelate can be greatly enhanced by modifications of the EDTA molecule (Yeh, S., D. Sherman, et al., *Anal Biochem.*, 100: 152–159, 1979). The simplest initial approach was to study the fluorescence characteristics of the chelate between Eu and other already commercially available polyaminopoly bis (2-aminoethyl ether) acetic acids. Ethylene glycol N,N,N',N'-tetraacetic acid (EGTA) has two aminoethyl ether groups. As a result of this molecular structure, EGTA should show similar energy absorption and transfer properties to those found in the β-diketones in addition to its strong metal chelating properties. As predicted, the chelate between europium and EGTA is fluorescent, eliminating the need for an additional enhancer. FIG. 5 also shows that the chelate maintains the narrow emission bands characteristic of Eu (590 nm and 613 nm).

One of the limitations of the EGTA lanthanide chelates, however, is that they are not as stable in aqueous solution as the polyazamacrocyclic lanthanide chelates are. For instance, the stability constant of EGTA-lanthanide complex is $10^7$, while the stability constant of the polyazamacrocyclic DOTA-lanthanide chelates is several orders of magnitude higher ($K=10^{20}$) (Bousquet, J., S. Saini, et al., *Radiology*, 166: 693–698, 1988). Since there is a close correlation between in vitro stability and in vivo safety (Bousquet, 1988), the lower stability constant of EGTA-lanthanide chelates may create some concern about possible toxic effects due to the deposition of free lanthanide in bone and soft tissue. Despite the striking differences in the stability constant, however, use of EGTA chelates in fluorescence studies is safer than the use of DOTA chelates in MRI studies. The reason for this apparent discrepancy is that, due to the high intrinsic sensitivity of the fluorescent techniques, the fluorescent agents are used as tracers, not as contrast agents. The required concentration of fluorescent agents is several orders of magnitude smaller than the concentration of DOTA chelates used in MRI contrast studies. Despite a higher safety factor, however, the potential toxicity of EGTA-chelates, especially after repeated doses, remains a concern.

Chelating agents based upon tetraazamacrocyclic backbones have proven to be extremely valuable for generating aqueous stable lanthanide chelates. The superior nature of this class of chelates has made them useful for diagnostic and therapeutic medical applications. For example, paramagnetic chelates of these compounds based upon gadolinium (Gd) are currently used as contrast agents for magnetic resonance imaging (MRI). Unfortunately, the current tetraazamacrocyclic chelates of Gd used in MRI are either very weakly fluorescent or exhibit no fluorescence at all. However, the addition of an aromatic moiety to the chelate can enhance luminescence. For example, a newly developed polyazamacrocyclic chelate incorporating a pyridine as the enhancer group exhibited fluorescence emission with a large difference between the excitation and emission wavelengths (>280 nm) and a high quantum yield of 0.51 (Costa, J. and R. Delgado, *Inorg. Chem.*, 32: 5257–5265, 1993; Kim, D., G. Kiefer, et al., *Inorg. Chem.*, 34: 2233–2243, 1995; Bornhop, D., D. Hubbard, et al., *Anal. Chem.*, 71: 2607–2615, 1999). Unfortunately, the flexibility of the macrocycle following the introduction of the pyridine moiety was partially lost while the orientation of the ester arms was affected by the asymmetry in the macrocycle. As a result, the affinity constant was even lower (k=19.5) than the value for DTPA (k=23) (Aime, S., M. Botta, et al., *J. Chem. Soc., Chem. Commun.*, 1995: 1885–1886, 1995). In addition, incorporation of the pyridine group, in conjunction with the substitution of the acetate groups for phosphonic acid n-butyl ester groups, resulted in an increase in the lipid solubility of the compound. As a result, the new molecule exhibits significant hepatic and bowel excretion in addition to renal excretion (Bornhop, 1999). The pharmacodynamic characteristics of this compound render it totally unsuitable for the present application. In contrast, for the instant invention, the starting reactants in the synthesis of the new agents are compounds with a well-recognized organ and function specificity.

Figure 6:
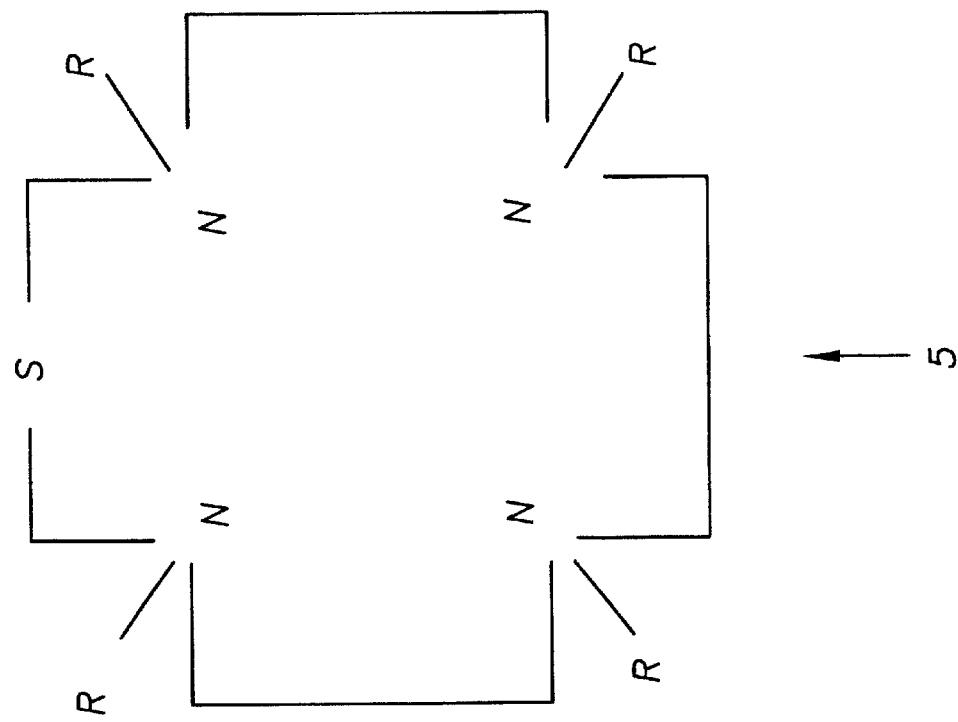
FIG. 6 depicts a macrocyclic compound according to an embodiment of the present invention.
Figure 7:
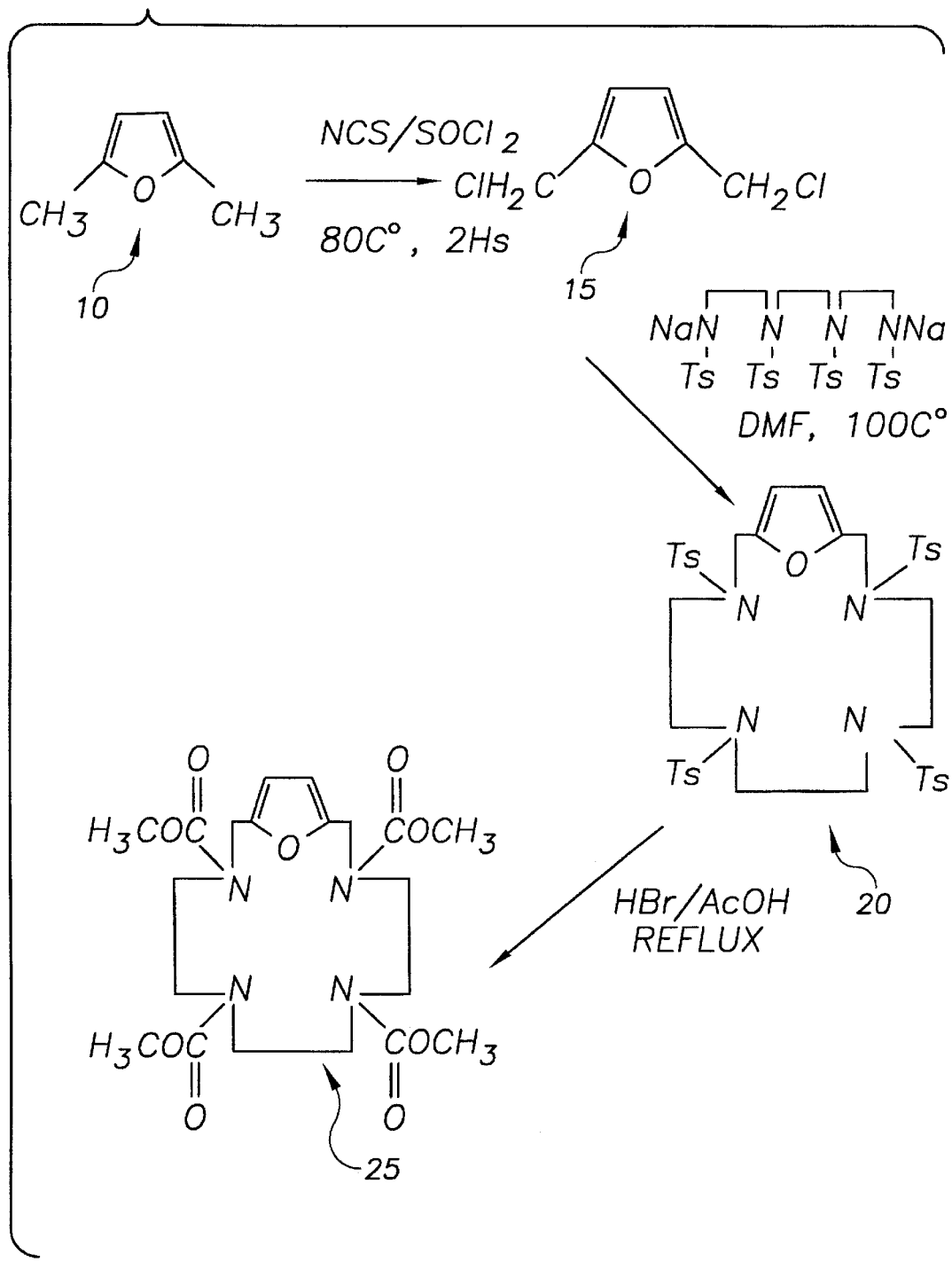
FIG. 7 depicts an exemplary synthetic pathway for production of TABFTA.

To increase chelate stability while retaining the advantages of the lanthanide chelates, a new GFR agent is proposed. The new fluorescent agent is based on lanthanide chelates derived from the polyazamacrocyclic compound of general formula (5), wherein the second cyclic group (S) is part of the macrocyclic backbone (FIG. 6). The second cyclic group (S) may be a furan, a tetrahydrofuran, a pyrrole, a pyrrolidine, or a derivative such as 3-furoic acid. Chelates derived from this family of macrocyclic ligands are among the most thermodynamically and kinetically stable lanthanide complexes, an important consideration for human studies where metal ion toxicity is a major concern. The compound of formula 25, tetraazabycyclofurantetraacetate (TABFTA) is very similar to the compound tetraazacyclododecane tetraacetic acid (DOTA) used as an MRI contrast agent (FIG. 7). As a result, it is anticipated that after intravenous injection, the chelates of TABFTA and a lanthanide such as neodymium will have biological characteristics similar to the chelates of DOTA and gadolinium, such as being excreted only by glomerular filtration and having an extracellular space distribution (Bousquet, 1988). In this concern, measurement of renal function and, in particular, glomerular filtration will be pursued without further structural modifications of TABFTA.

Figure 8:
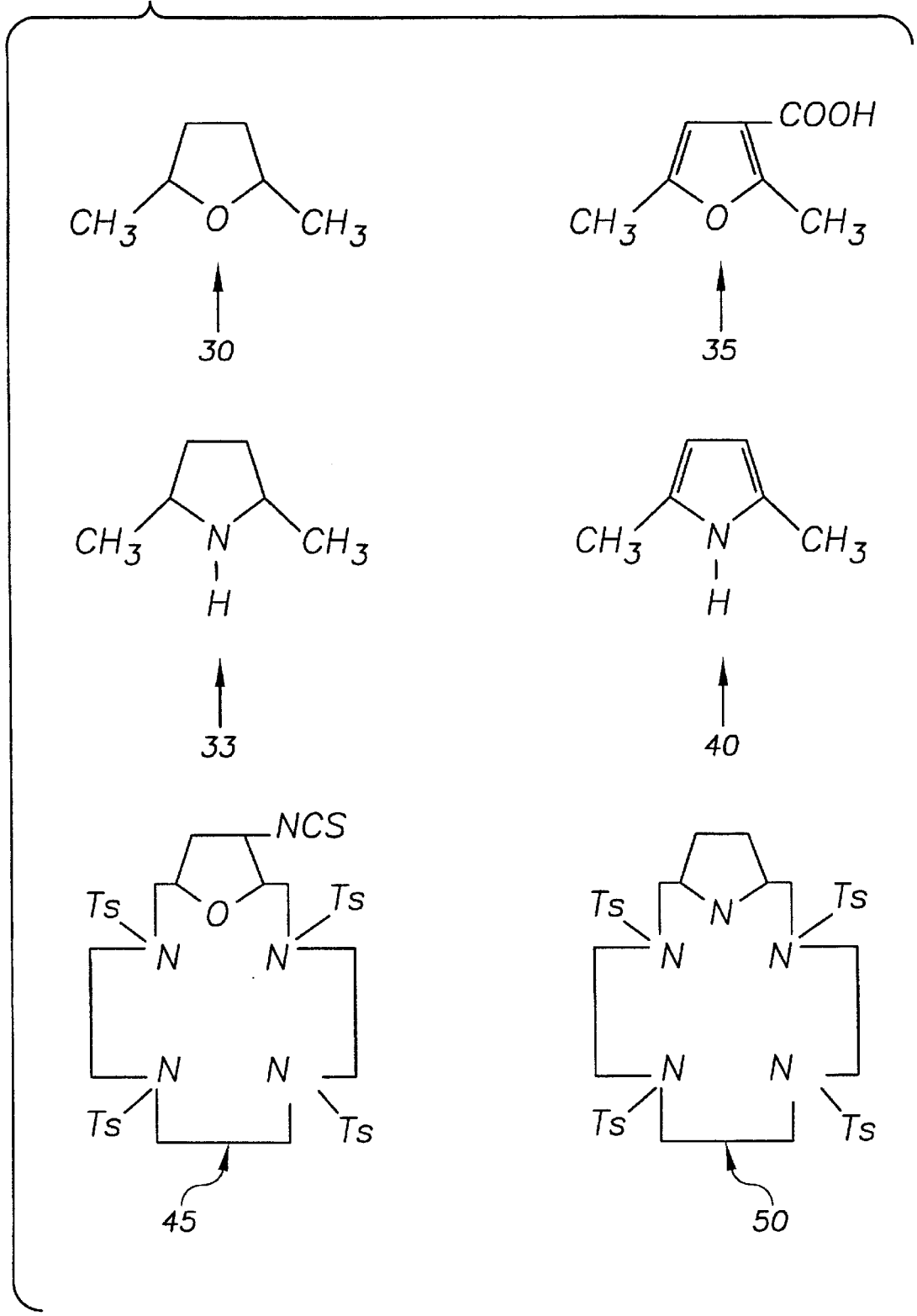
FIG. 8 displays exemplary starting materials, intermediates, and end products for use in the methods of the invention.

To take advantage of the low background interference of time-resolved fluorometry, TABFTA can also be used also as a bifunctional chelating agent for the labeling of antibodies, antibody fragments, hormones, hormone fragments, nucleic acids, neurotransmitters, or any other biologically active material. For example, TABFTA may be modified as depicted in formula 45 by introduction of a $NO_2$, NH2, isothiocyanato, semicarbazido, thiosemicarbazido, maleimido, bromoacetomido or carboxyl group in position 15 (FIG. 8).

Synthesis of chelate: The complexes are prepared by methods well known in the art (Dwyer and Mellor, *Chelating Agents and Metal Chelates*, Academic Press, 1964; Richman, J. and T. Atkins, *J. Am. Chem. Soc.*, 96: 2268–2270, 1974). All the reactants are commercially available. FIG. 7 provides a detailed description of the preparation of one of the compounds of this invention, a 15-member tetraazamacrocyclic structure possessing one dimethylfuran moiety. 2,5-dimethylfuran (10) is first converted to the chloromethyl derivative (15). In a separate step, triethylenetetraamine is tosylated and converted to the sodium salt. These two reagents are then combined in DMF to give the N-tosylated macrocycle (20) (Richman, 1974). Heating the product in a mixture of acetic acid (AcOH) and HBr provides a protecting group to the amine groups. The tetraacetic derivative (25) is then synthesized by reacting the secondary amines of the macrocycle with chloroacetic acid as described by Desreux (Desreux, J., *Inorg. Chem.*, 19: 1319–1324, 1980).

The second cyclic group S may be varied to modify the electron density of the molecule and the electron distribution along the backbone. For example, compound 10 can be replaced with 2,5-dimethyltetrahydrofuran (30), 2,5-dimethylpyrrolidine (33), 2,5-dimethyl-3-furoic acid (35), or 2,5-dimethylpyrrole (40). Use of compound 15 results in production of compound 50 instead of compound 20 as an intermediate. One skilled in the art will see that a number of different substituents, such as the isothiocyanate group in compound 45, can be placed on the molecule by an appropriate choice of precursor for cyclic group S.

Treatment of these compounds with a lanthanide acetate yields the desired fluorescent chelate. Neodymium, terbium or europium acetate (0.1M) and an equimolar amount of tetraazacycloalkene N, N', N'', N'''' derivative are mixed in water at 80° C. The pH of the solution is adjusted to 10 by addition of concentrated $NH_4OH$ and the mixture stirred for 20 h. After filtration, the cooled reaction solution is evaporated to a solid and dried overnight in a vacuum oven to sublime the byproduct, ammonium acetate.

Detection: All the components for the assembly of an instrument for TFM are commercially available and have been tested extensively in everyday applications. The essential components of the instrument are the following:

a) the fluorescence excitation system;

b) the fluorescence detection system; and c) the operating system and data logger.

a. The fluorescence excitation system: The excitation system may incorporate either high intensity light-emitting photo diodes or laser diodes. These components have several properties that make them ideal for the present application by increasing safety and portability. They are current sensitive devices with low-power output, low operating voltage, and high-frequency response. Both types of diodes are very small and can be battery-operated with input power of 3.5 to 5.0 VDC and only 50–100 mA input currents.

For standard fluorometry, a better match between the dye excitation wavelength and the component emission wavelength can be obtained with the high intensity light-emitting photo diodes than with laser diodes. High intensity, light-emitting photo diodes offer a broad selection of wavelengths from which a specific wavelength can be selected to better match the excitation wavelength of the fluorescent dye. For time-resolved fluorometry with neodymium chelates, however, laser diodes with an emission wavelength of 830 nm are preferred because their emission wavelength is a perfect match for the excitation wavelength of the lanthanide.

Both light sources have the advantage of very high frequency response. Thus, the emitted light beam can be pulsed with a regulated electronic pulse generator by turning the source on and off. This electronic gating system offers several advantages over the mechanical system, including better control of the frequency, duration, and intensity of the light pulses. For GFR agents labeled with laser dyes, the emitted light intensity measurements are performed during pulses; for lanthanide chelates, the measurements are performed between pulses, after the background fluorescence has decayed to minimal values.

Figure 10:
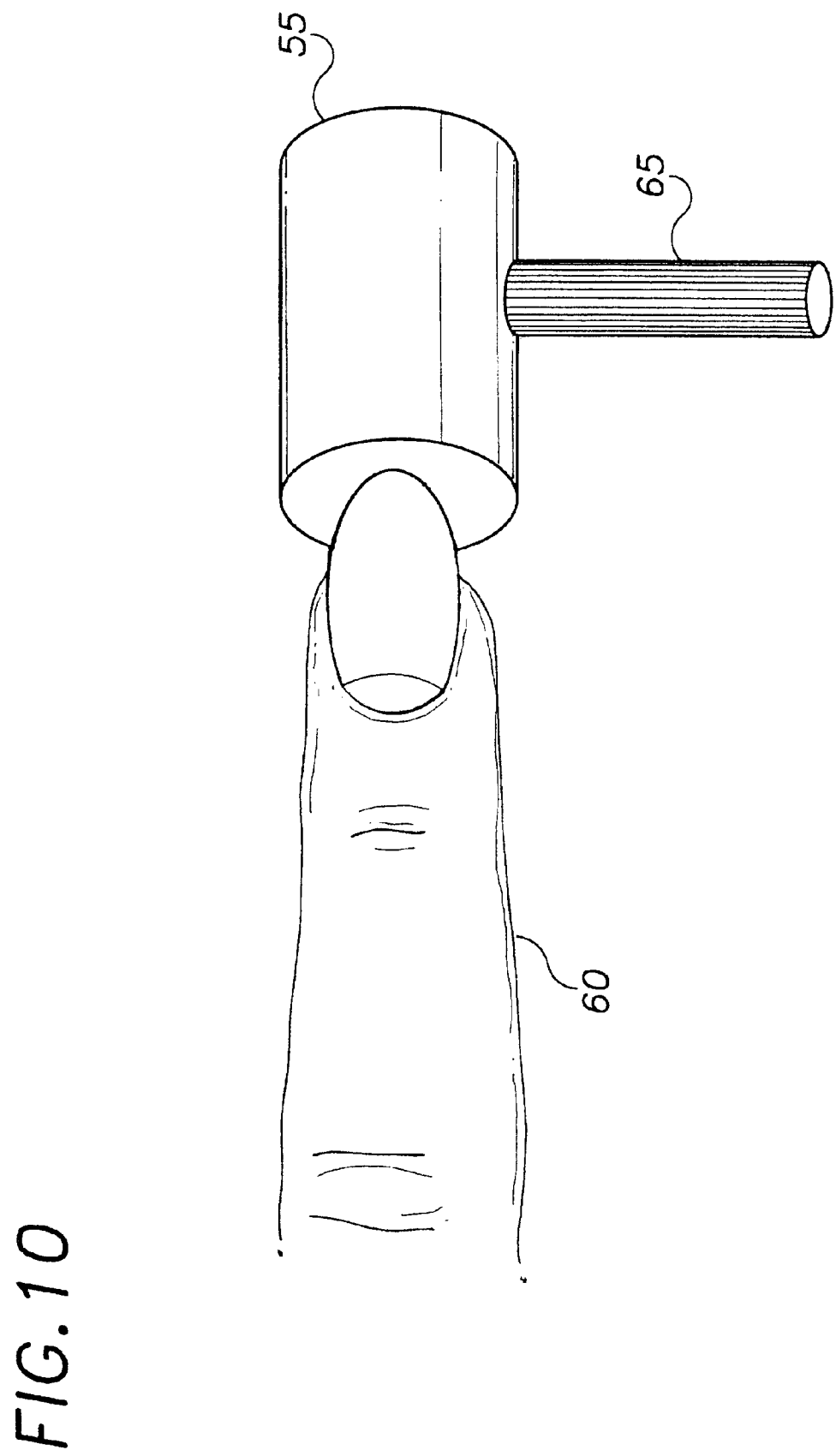
FIG. 10 illustrates a finger sleeve with which an apparatus according to the invention can be operated.

Separation of the excitation from the emission beam is accomplished by using long wave pass filters, whose small size and weight increase portability. A diagram of the system is displayed in FIG. 3. Filters with an appropriate cut-on wavelength are selected for the specific fluorescent agent in use, e.g., 850±7 nm (for neodymium-chelates) or 700±6 nm (for indocyanine green-EDTA or oxazin-EDTA). The 850 nm filter should reflect and re-direct a 830 nm beam from the laser source to the tissue while allowing full transmission of the 1,050 nm and 1,350 nm emission bands of neodymium-chelates. Similarly, the 700 nm filter should reflect and re-direct the 420–600 nm beam from the high intensity light-emitting photo diodes to the tissue while allowing full transmission from the tissue to the detector unit of the emission beam of the indocyanine green-EDTA or oxazin-EDTA. The excitation pulses are launched into single or multiple 2000 μm core-diameter fused silica optical fibers or liquid core lightguides with a 5 mm focal length lens. After a proximal short circular arrangement, the fibers are rearranged linearly to obtain a structure similar to a short band 55 (FIG. 10). This excitation band is placed and secured over the skin or mucosa of a body part, for example, finger 60, to excite the tissue underneath. The volume of the excited tissue is changed by adjusting the intensity of the excitation beam or the number and/or core diameter of the liquid lightguides or silica optical fibers 65.

A serious concern with the present technology is that the use of laser beams may result in tissue damage. However, this possibility can be eliminated or at least minimized by incorporating four important features into the design of the instrument. First, excitation is accomplished with the use of laser diodes with very low power output (i.e., 2–5 mW) to avoid exceeding an exposure rate of 0.003 J/cm$^2$. Second, the excitation beam is pulsed with an electronic pulse-generator to excite the tissue with very short laser pulses of only a few nanoseconds duration. Third, the wavelength of the excitation beam is always maintained over 420 nm. Finally, conduction of the excitation beam is performed with large core fiber optic bundle to distribute the excitation laser beam over a large area. The low power and short pulses of the excitation beam should also reduce the possibility of photobleaching frequently observed with the use of standard fluorescent dyes.

b. The detection system: Fluorescence from the skin or mucosa and deeper tissues will be collected by the excitation band and conducted through liquid lightguides or silica optical fiber to the long wave pass filter. The filter facilitates separation of the emission and excitation beams and reduces background contribution, as disclosed above. Fluorescence transmitted through the filter is recorded using an intensified photodiode array or IR detector for variable integration times. The intensifier/detector unit is electronically gated to measure the fluorescence intensity emitted during (for standard fluorometry) or a time after (for time resolved fluorometry) the excitation pulse.

c. The operating system and data logger: Tattletale® data loggers designed by Onset Computer are used to operate the system and record fluorescence vs. time. Several characteristics of this data logger make it ideal for the present application. The data file size for this series ranges between 8 to 224 Kb, more than sufficient to allow the instrument to perform all its expected functions. All the models available are battery-operated, low power system with drains between 2 to 3 mA. In addition, all the Onset Computer's Tattletale® loggers are pocket-sized, lightweight, sturdy units. The data logger, along with the batteries necessary to operate the system and the detector, are housed in a pocket-sized plastic box. The loggers are assembled with an alphanumeric display to show the updated rate constant value at pre-set intervals. This feature is extremely useful in acute situations such as operating rooms and intensive care units. The data loggers also have sufficient memory to determine the instant value of this constant for a long period of data collection.

Operation: The excitation/detector unit of the instrument is affixed to the skin covering a body part such as a fingertip or a section of the arm or to the nasal or oral mucosa of the patient. Organ function is then measured in real time as rate of depletion in tissue of a fluorescent agent that is cleared exclusively by that particular organ. In other terms, organ function is measured as the efficiency with which a particular organ removes a function-specific fluorescent agent from the tissue. The rate of depletion of the agent is measured from the change in the individual transcutaneous fluorescence measurements over time. The individual transcutaneous tissue fluorescence measurements are performed by integrating the emitted tissue fluorescence for a very short period of time (50 nsec to 100 msec) during (standard fluorometry) or after (time-resolved fluorometry) the excitation pulse. Since the excitation pulses are very short, the individual fluorescence measurements may be performed very frequently with minimal interruption between measurements. The rate of excretion is then determined by plotting the individual transcutaneous fluorescence measurements with respect to time for very short time intervals (2 to 5 minute intervals) after a bolus intravenous injection of the tracer. Since the system response follows first-order kinetics (Rabito, 1994), the slope of the correlation between the log of the individual fluorescence intensity measurements vs. time represents the rate constant of the system. The data collected is subjected to repetitive, on-line, least squares analysis to obtain the best fit between the log of fluorescence intensity (in arbitrary units) versus time (in minutes) at intervals of 2 to 5 minutes. After arrival, the new data is processed and added to the correlation to obtain a continuous update of the line. Analysis of co-variance (ANOVA) is used to assess the differences between the slope (rate constant) for the previous and the current 2 to 5 minute intervals. Thus, a rate constant and its corresponding statistical value can be generated almost continuously. Decreases or increases in the rate constant value are considered to represent decreases or increases in GFR when the patient is injected with a fluorescent GFR agent.

Although current data loggers have the computer power necessary to determine the value of this constant on the instrument, the data can also be transferred to a dedicated personal computer. After transferring the data, the required curve fitting and complete analysis is carried out by using a commercially available statistics software package.

Software: The basic software for the operation of the unit is a modification of the program developed initially for the renal monitor that works with radioactive tracer (Rabito, 1994). The program is designed to control the type of excitation to be used (continuous or pulse excitation), duration of the excitation pulse, interval between pulses, the time between the excitation pulse and the measurement of the emission signal, and the integration period for the measurement of the emission signal. For standard fluorescence determination, the emitted fluorescence intensity is measured during each pulse. For time-resolved fluorescence measurements, however, the operating program is set to integrate the emission signal a few microseconds after the laser pulse to allow for full background decay. The analysis software is based on the single compartment model described by Brochner-Mortensen (Brochner-Mortensen, J., *Scand. J. Clin. Lab. Invest.*, 30: 271–276, 1974) as was previously published (Rabito, 1994).

Conclusions—Real-Time Renal Monitoring: FARM has several definite advantages over the radioactive monitoring technique described in the Background. First, the technique will eliminate the use of radioactivity with all its intrinsic limitations. Second, FARM can be assembled with more standard components than the radioactivity detectors. For instance, the laser diodes and laser detectors are very inexpensive ($50 to $125) and widely available laser components that have been tested extensively in everyday applications such as CD players, printers, facsimile machines, laser security fences, etc. On the contrary, the cadmium-telluride detectors for monitoring radioactive tracers are available from only two manufacturers in the USA, at a cost that is about 15 times higher ($2,500) than the laser components. Another advantage of FARM is that, as a result of a simpler design, the patient will be more comfortable wearing the instrument for extended periods of time. For example, the excitation/detection system of FARM can be arranged in a finger sleeve which is more comfortable and less bulky than the heavy lead-lined arm sheaths used in the radioactivty assay. FARM can also be used for multi-label assays in which different fluorophores having different emission wavelengths are used simultaneously.

In FARM, the fluorescent signal originates solely in the tissue volume excited by the laser beam (Frisoli, 1993), eliminating the scattered activity from adjacent body structures commonly found with the radioactive method and obviating the need for special shielding. This attribute should result in a significant decrease in the total weight of FARM and more comfort for the patient, especially during prolonged monitoring of renal function. Two other important advantages of FARM over the radioactive technique are that the tissue volume probed during measurement remains relatively constant, and that the size of this volume can be adjusted by changing the excitation wavelength. This feature permits adjustment of the sensitivity of the instrument to a particular need without changing the dose of the fluorescent agent injected.

In conclusion, FARM, especially when conducted with the novel molecules disclosed herein, provides a reliable method for real-time monitoring of renal function. This technique, in conjunction with appropriate agents, may be exploited to monitor metabolic function for other organs as well. It provides a powerful tool for health care providers to quickly identify patients experiencing kidney or other organ failure and apply appropriate remedies.

Immunoassay: The molecules of the invention can also be used as labels for bioanalytical assays. The molecules can be attached to specific binding reagents, or ligands, for a variety of analytes. For example, they can be attached to antibodies for use in immunoassays, DNA or RNA fragments for hybridization assays, or enzyme or enzyme cofactors for enzyme assays. The molecules may be directly attached to the specific binding agent for the analyte or may be attached to a more general binding agent that acts as a secondary label. In the latter case, the secondary agent binds to a primary specific reagent. In another embodiment, the analyte may be immobilized on a substrate, following which the specific binding agent labeled with the luminescent molecule is allowed to bind to the analyte. The labeled agent may be attached to the analyte and excess unbound agent washed away. At this point, the molecule may be separated from the specific binding agent. The concentration of the molecule will still reflect the quantity of analyte; however, the concentration of the molecule can be measured in solution instead of an immobilized solid phase.

Alternatively, the metal ion may be chelated to a non-luminescent label attached to the specific binding agent. After the excess agent is rinsed away, only the metal atom is detached, for example, by changing the pH of the solution. The metal ion is then solubilized into a micelle carrying the organic chelate which binds a metal ion to form a luminescent complex. Suitable micellar materials include Triton X-100 (CAS 9002-93-1, available from Sigma-Aldrich, Inc.) detergent in phosphate buffer. Once the metal ion is separated from the labeling chelate, for example, EDTA or DTPA, it is incorporated into the micelle. Because unchelated lanthanides do not emit particularly intensely, the micelles also contain a chelating agent such as the molecules of the instant invention. This method has been commercialized using Eu as the metal ion and β-naphthoyltrifluoracetone (NTA) and trioctylphosphine oxide (TOPO) as the chelate. Multiple antigens can be detected simultaneously by using different ions to label each.

All of these detection methods are well known in the art and are described, for example, in the review article by Dickson, et al. (Dickson, E. F. G., A. Pollak, et al., *J. Photochem. Photobio. B*, 27: 3–19, 1995). However, currently available fluorescent labels incorporating lanthanide ions suffer from low luminescence yield, low chelate stability, and low solubility in aqueous media. The lanthanide chelates disclosed herein were originally optimized for detection in blood, an aqueous medium, and are suitable for detection in other aqueous solutions. They also offer high affinity constants and luminescence yields (quantum efficiency ($\phi$=0.2–0.5).

Magnetic Resonance Imaging Contrast Agent: The molecules of the invention, especially TABFTA and its derivatives, can also be used as contrast agents for magnetic resonance imaging (MRI). When chelated with lanthanide ions such as gadolinium ($Gd^{3+}$) or technetium ($Tc^{2+}$), the resulting paramagnetic compound enhances the relaxation of hydrogen protons, increasing signal intensities in MRI imaging (Bousquet, 1988). The increased signal increases the signal-to-noise ratio, reducing imaging time. In addition, the contrast agent may increase specificity in diagnosis. Because TABFTA is water-soluble, the complex can be used as a contrast agent in blood, for example, to measure blood flow in patients at risk for stroke or other circulatory malfunctions. Of course, the agent can also be used to image the functioning of the kidneys and bladder.

The performance of MRI on a patient is well understood by those skilled in the art. A patient is exposed to a high powered magnetic field, following which a radio frequency pulse is applied and absorbed by a small portion of the patient's hydrogen ions. The pulse changes the spin state of the protons; once the RF pulse is removed, the protons relax to their original spin state, releasing stored energy, which can be detected by the MRI apparatus. The contract agent is injected into the patient before exposure to the magnetic field. As noted above, the agent improves the performance of the apparatus.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method of detecting a clearance function in a subject comprising:

providing an electroluminescent agent in a circulatory system of the subject;

irradiating a tissue site with electromagnetic radiation having sufficient energy and intensity to be absorbed by the agent;

detecting the intensity of emission from the tissue site; and repeating the step of detecting at known time intervals, wherein:

the agent comprises an electroluminescent moiety conjugated with

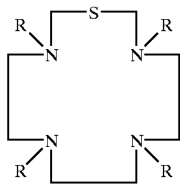

wherein S is a five-membered cyclic organic moiety having at least one atom selected from oxygen and nitrogen, and wherein R is an organic acid.

2. The method of claim 1, further comprising irradiating the tissue site with a laser.

3. The method of claim 2, wherein the step of repeating is performed until an elapsed time since the step of irradiating is about 90% of the decay time.

4. The method of claim 2, wherein the laser is pulsed.

5. The method claim 2, further comprising waiting until a background emission has decayed to an insignificant level before performing the step of detecting.

6. The method of claim 1, wherein the electroluminiscent agent has a decay time of greater than 50 ns.

7. The method of claim 6, wherein after the step of detecting has been repeated a predetermined number of times, the step of irradiating is repeated.

8. The method of claim 1, wherein the agent is cleared exclusively by the glomerulus.

9. The method of claim 1, wherein the conjugate exhibits fluorescence when irradiated with red or infrared light.

10. The method of claim 1, wherein the electroluminescent moiety is a lanthanide ion.

11. The method of claim 10, wherein the lanthanide ion is trivalent.

12. The method of claim 11, wherein the lanthanide ion is selected from the group consisting of $Ce^{3+}$, $Nd^{3+}$, $Sm^{3+}$, $Eu^{3+}$, and $Tb^{3+}$.

13. The molecule of claim 1, wherein S is a member of furanyl, tetrahydrofuranyl, pyrrolidinyl, furoyl, pyrrolyl, and any of the above substituted with a member of $NO_2$, $NH_2$, isothiocyanato, semicarbazido, thiosemicarbasido, maleimido, bromoacetomido, and carboxyl group.

14. The molecule of claim 1, wherein R is an acetate or a p-toluene sulfonyl group.

* * * * *